(12) United States Patent
Lambin et al.

(10) Patent No.: US 10,311,571 B2
(45) Date of Patent: Jun. 4, 2019

(54) IMAGE ANALYSIS METHOD SUPPORTING ILLNESS DEVELOPMENT PREDICTION FOR A NEOPLASM IN A HUMAN OR ANIMAL BODY

(71) Applicant: Stichting Maastricht Radiation Oncology, Maastricht (NL)

(72) Inventors: Philippe Lambin, Maastricht (NL); Sara Joao Botelho de Carvalho, Maastricht (NL); Ralph Theodoor Hubertina Leijenaar, Maastricht (NL)

(73) Assignee: Stichting Maastricht Radiation Oncology "Maastro-Clinic", Maastricht (NL)

( * ) Notice: Subject to any disclaimer, the term of this patent is extended or adjusted under 35 U.S.C. 154(b) by 0 days.

(21) Appl. No.: 15/519,290

(22) PCT Filed: Oct. 17, 2014

(86) PCT No.: PCT/NL2014/050728
§ 371 (c)(1),
(2) Date: Apr. 14, 2017

(87) PCT Pub. No.: WO2016/060557
PCT Pub. Date: Apr. 21, 2016

(65) Prior Publication Data
US 2017/0236283 A1    Aug. 17, 2017

(51) Int. Cl.
*G06T 7/00* (2017.01)
*G06K 9/62* (2006.01)
(Continued)

(52) U.S. Cl.
CPC .......... *G06T 7/0016* (2013.01); *A61B 5/0095* (2013.01); *A61B 5/015* (2013.01);
(Continued)

(58) Field of Classification Search
USPC ........................................................ 382/131
See application file for complete search history.

(56) References Cited

U.S. PATENT DOCUMENTS

| | | | | |
|---|---|---|---|---|
| 5,840,507 A | * | 11/1998 | Fruehauf | G01N 33/57484 435/7.23 |
| 9,317,781 B2 | * | 4/2016 | Tu | G06K 9/6259 |

(Continued)

FOREIGN PATENT DOCUMENTS

WO    WO 2006/078902 A2    7/2006

OTHER PUBLICATIONS

Fergus et al., "Assessment of Tumor Heterogeneity: An Emerging Imaging Tool for Clinical Practice?," Insights Into Imaging, vol. 3, No. 6 (Dec. 1, 2012) pp. 573-589.

(Continued)

*Primary Examiner* — Jerome Grant, II
(74) *Attorney, Agent, or Firm* — Leydig, Voit & Mayer, Ltd.

(57) ABSTRACT

The present invention relates to an image analysis method for providing information for supporting illness development prediction regarding a neoplasm in a human or animal body. The method includes receiving for the neoplasm first and second image data at a first and second moment in time, and deriving for a plurality of image features a first and a second image feature parameter value from the first and second image data. These feature parameter values being a quantitative representation of a respective image feature. Further, calculating an image feature difference value by calculating a difference between the first and second image feature parameter value, and based on a prediction model deriving a predictive value associated with the neoplasm for supporting treatment thereof. The prediction model includes a plurality of multiplier values associated with image features. For calculating the predictive value the method (Continued)

includes multiplying each image feature difference value with its associated multiplier value and combining the multiplied image feature difference values.

15 Claims, 9 Drawing Sheets

(51) Int. Cl.
 G06K 9/52 (2006.01)
 A61B 5/00 (2006.01)
 A61B 5/01 (2006.01)
 A61B 5/055 (2006.01)
 A61B 6/03 (2006.01)
 A61B 6/00 (2006.01)
 A61B 8/08 (2006.01)
(52) U.S. Cl.
 CPC ............ A61B 5/055 (2013.01); A61B 5/7275 (2013.01); A61B 6/032 (2013.01); A61B 6/037 (2013.01); A61B 6/5235 (2013.01); A61B 6/5247 (2013.01); A61B 8/085 (2013.01); G06K 9/527 (2013.01); G06K 9/629 (2013.01); G06K 2209/053 (2013.01); G06T 2207/10072 (2013.01); G06T 2207/10104 (2013.01); G06T 2207/20064 (2013.01); G06T 2207/20076 (2013.01); G06T 2207/30024 (2013.01); G06T 2207/30096 (2013.01)

(56) References Cited

U.S. PATENT DOCUMENTS

| 2010/0254584 | A1 | 10/2010 | Gulsun et al. | |
| 2010/0316990 | A1* | 12/2010 | Dynan | G01N 33/57411 435/5 |
| 2012/0070060 | A1* | 3/2012 | Mahato | G06K 9/00127 382/133 |
| 2013/0172203 | A1* | 7/2013 | Yeatman | C12Q 1/6886 506/9 |
| 2016/0078613 | A1* | 3/2016 | Lambin | G06K 9/0014 382/131 |
| 2016/0312292 | A1* | 10/2016 | Trotter | C12Q 1/6886 |
| 2017/0184565 | A1* | 6/2017 | Roberts | G01N 33/5011 |
| 2017/0213067 | A1* | 7/2017 | Padmanabhan | G06K 9/0014 |
| 2017/0330315 | A1* | 11/2017 | Okuda | G06T 7/001 |
| 2018/0011100 | A1* | 1/2018 | Satake | G01N 33/57426 |

OTHER PUBLICATIONS

Gunasundari, et al., "A Study of Textural Analysis Methods for the Diagnosis of Liver Diseases from Abdominal Computed Tomography," International Journal of Computer Applications, vol. 74, No. 11 (Jul. 1, 2013) pp. 7-12.

European Patent Office, International Search Report in PCT International Application No. PCT/NL2014/050728 dated Jul. 13, 2015.

* cited by examiner

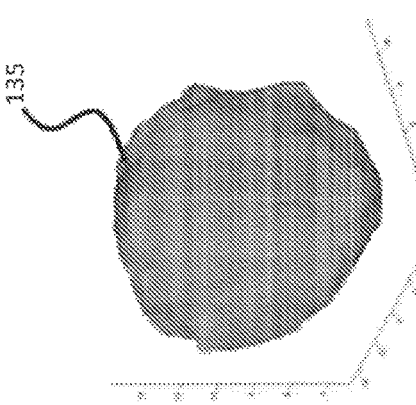
| Volume | 56.16 |
| Max. diameter | 9.14 |
| Surface | 136.94 |
| SVR | 2.44 |
| Sphericity | 0.52 |
| SD | 0.55 |
| Compactness (1) | 1.19 |
| Compactness (2) | 0.14 |
Fig. 2A-2
| Volume | 120.12 |
| Max. diameter | 13.40 |
| Surface | 98.99 |
| SVR | 0.74 |
| Sphericity | 0.85 |
| SD | 0.01 |
| Compactness (1) | 6.03 |
| Compactness (2) | 0.43 |
Fig. 2B-2
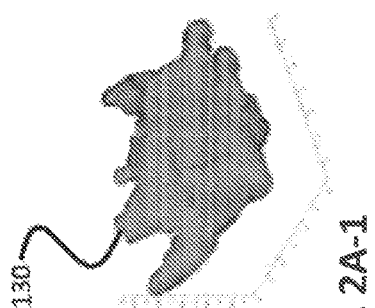
Fig. 2A-1
Fig. 2B-1

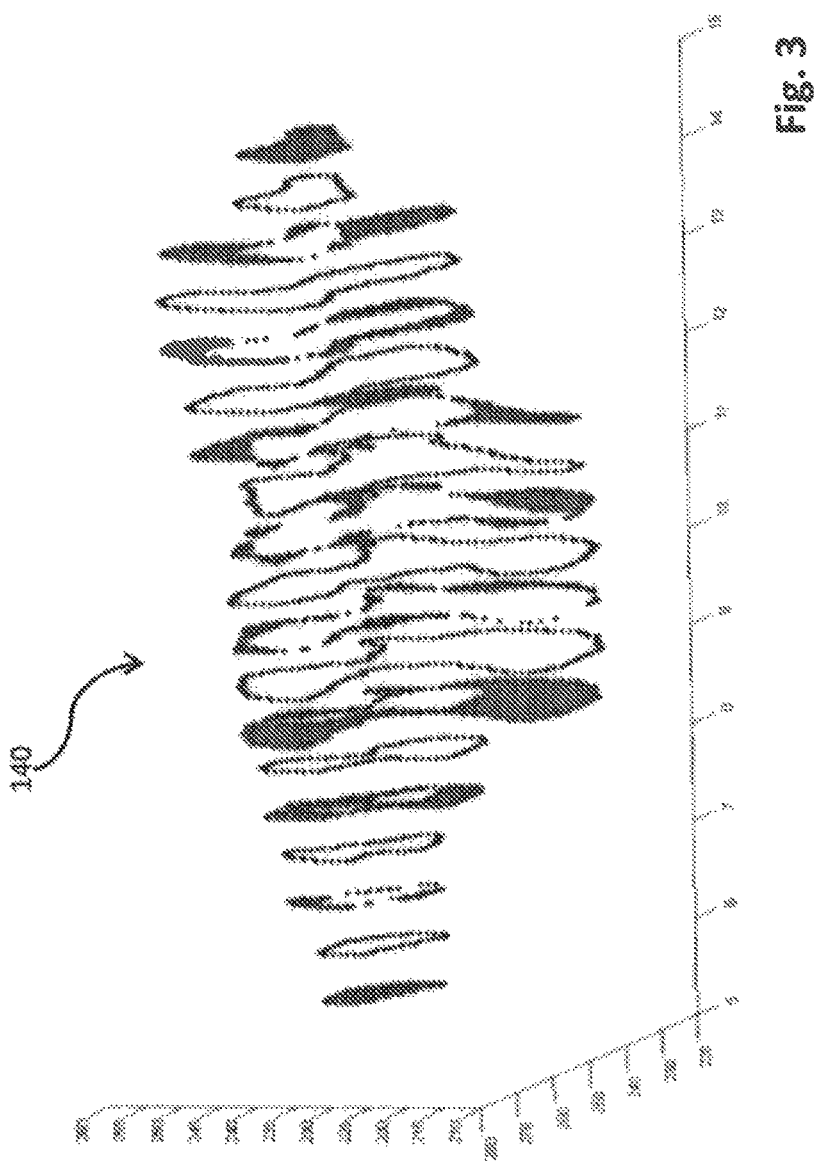

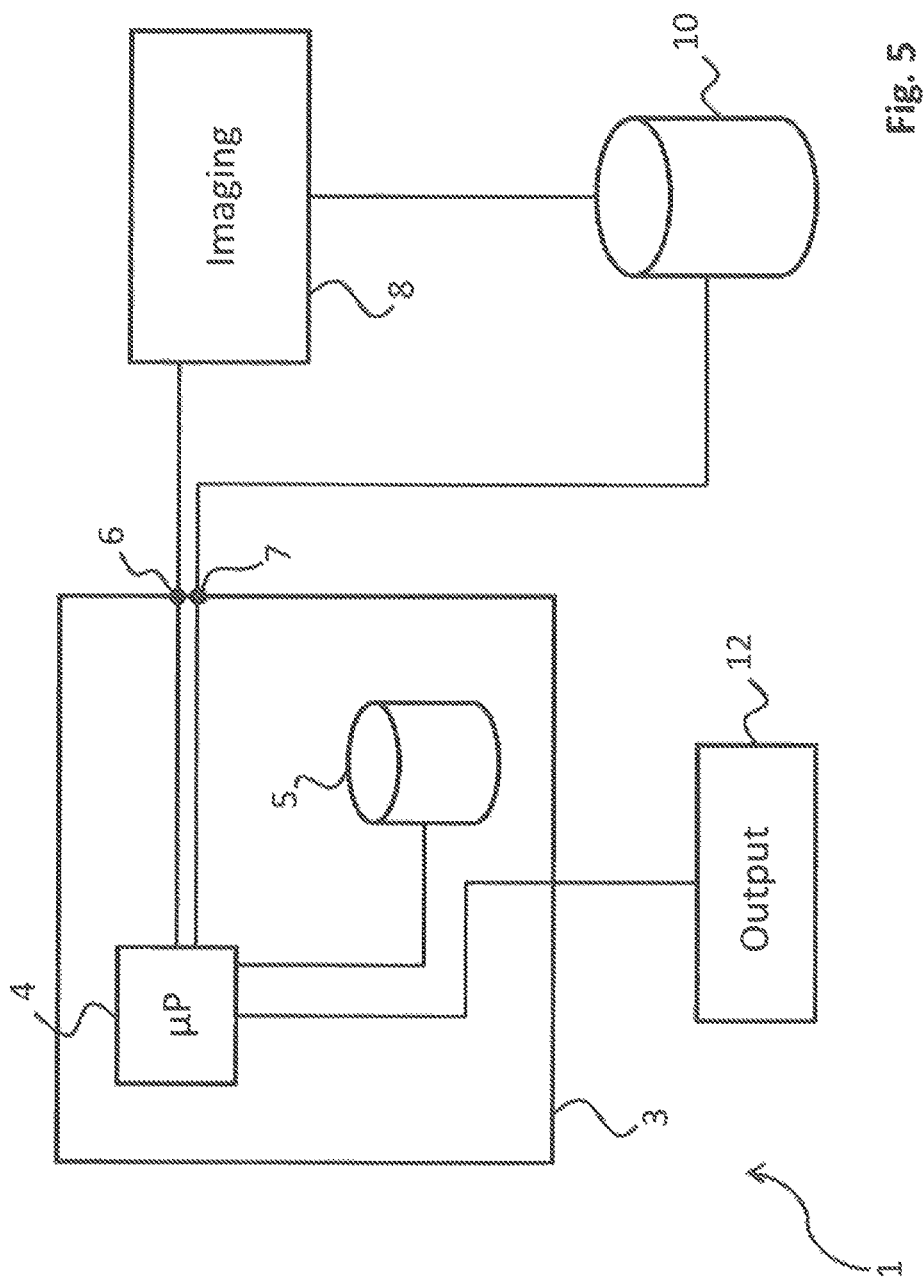

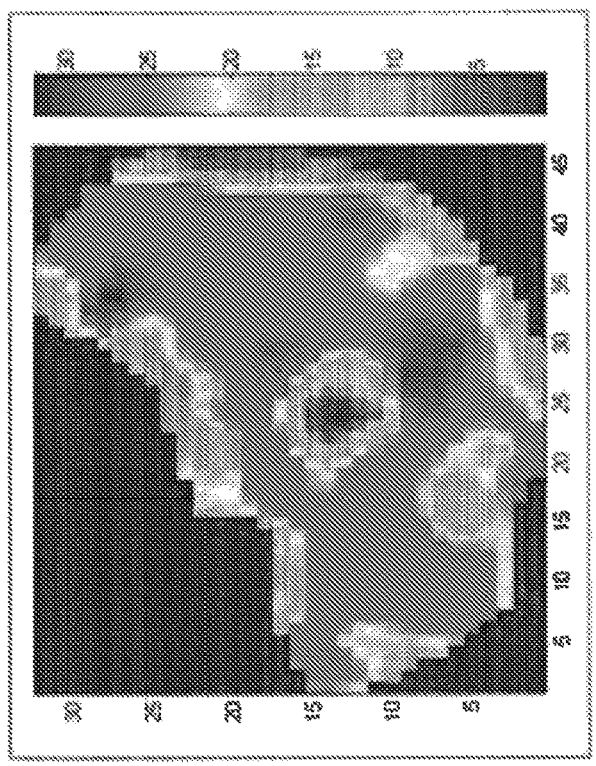
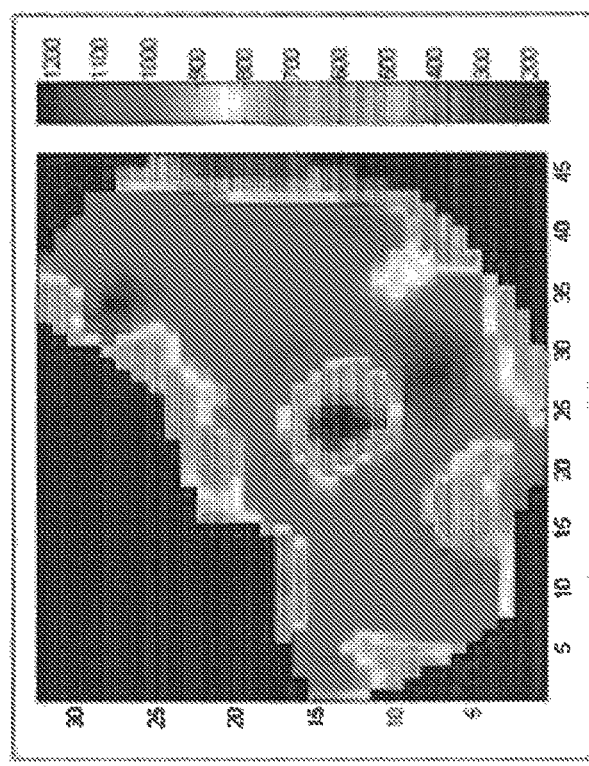
Fig. 8

IMAGE ANALYSIS METHOD SUPPORTING ILLNESS DEVELOPMENT PREDICTION FOR A NEOPLASM IN A HUMAN OR ANIMAL BODY

CROSS-REFERENCE TO RELATED APPLICATIONS

This patent application is a U.S. National Phase of PCT International Application No. PCT/NL2014/050728, filed Oct. 17, 2014, the contents of which is expressly incorporated herein by reference in its entirety, including any references therein.

FIELD OF THE INVENTION

The present invention relates to an image analysis method for providing information for supporting illness development prediction regarding a neoplasm in a human or animal body. The invention further relates to a decision support system, and to a computer program product and a computer readable medium comprising a computer program product.

BACKGROUND

Non-invasive imaging is one of the major factors that propelled medical science and treatment over the past decades. By assessing the characteristics of human tissue, imaging is often used in clinical practice for oncologic diagnosis and treatment guidance. A key goal of imaging is personalized medicine, were the treatment is tailored towards the specific characteristics of the patient. For personalized medicine, recent developments in the fields of genomics and proteomics have enabled the molecular characterization of tissue, such as neoplasms (i.e. tumors). However, as tumors are spatially and temporally heterogeneous, these techniques are limited, as they require biopsies or invasive surgeries to extract part of the tissue under study. Therefore, imaging can be of large importance as imaging can capture intra-tumoral heterogeneity, is already performed in routine practice, is non-invasive, and can be acquired during time.

Probably the most widespread imaging modality is computed tomography (CT), assessing the density of the tissue. Moreover, also positron emission tomography (PET) is a common imaging method applied in diagnosis and treatment of tumors. Positron emission tomography is based on the use of a radioactive tracer, i.e. a positron-emitter. For example a patient is given an injection of a small amount of a radioactively labelled glucose. Cancer cells capture more glucose than most of other tissues in the body, thereby enabling detection and imaging of the tumor. To enable treatment by means of personalized medication, it is highly desired to obtain information on treatment effectiveness of a followed treatment plan. As may be appreciated, early detection of an ineffective treatment enables a physician to review and modify the personalized medication at an early stage. The sooner an effective treatment is identified, the higher will be the chance on success of the treatment.

SUMMARY OF THE INVENTION

The following presents a simplified summary in order to provide a basic understanding of some aspects described herein. This summary is not an extensive overview. It is not intended to identify key or critical elements of the disclosure or to delineate the scope of the disclosure. The following summary merely presents some concepts directed to techniques for image analysis of imaging data of a human or animal neoplasm (i.e. a tumor), in a simplified form as a prelude to the more detailed description provided below.

The term "neoplasm" as used in this document is to be interpreted as an abnormal mass of tissue as a result of neoplasia, i.e. the abnormal growth or division of cells. The term neoplasm includes tumors, which form a particular type of neoplasms. Since the teachings of the present document are likely to be applied primarily to image analysis of tumors in research to and treatment of cancer, the neoplasms will throughout the text in many occasions be referred to as tumors. However, it is to be understood that the image analysis method of the present invention may potentially be applied to the imaging of other neoplasms, such as for example fibroids.

It is an object of the present invention to provide an image analysis method for deriving a predictive value usable as decision support value to a physician to enable early detection of treatment effectiveness.

These and other objects of the invention have been achieved in that there is provided an image analysis method in accordance with claim 1.

The invention relates to an image analysis method for providing information for supporting illness development prediction regarding a neoplasm in a human or animal body. The method comprises the steps of: receiving, by a processing unit, image data of the neoplasm, wherein said receiving comprises the steps of receiving first image data of the neoplasm at a first moment in time and receiving second image data of the neoplasm at a second moment in time; deriving, by the processing unit, for each of a plurality of image features associated with the neoplasm, a first image feature parameter value from the first image data and a second image feature parameter value from the second image data, said first and second image feature parameter value being a quantitative representation of said respective image feature at said first and second moment in time respectively; and calculating, by the processing unit, for each of the plurality of image features, an image feature difference value by calculating a difference between the first and second image feature parameter value for said respective image feature. Moreover, the method further includes deriving, by said processing unit using a prediction model, a predictive value associated with the neoplasm for supporting treatment thereof, wherein said prediction model includes a plurality of multiplier values, each multiplier value being associated with an image feature for multiplying an associated image feature difference value therewith, wherein for calculating the predictive value the method includes multiplying each image feature difference value with its associated multiplier value and combining the multiplied image feature difference values such as to obtain the predictive value for the neoplasm.

Suitable combination of a number of selected image features enables to distinguish specific phenotypes of neoplasms from each other. The present invention is based on the insight that a subset of specifically selected image features taken from image data of the tumor or neoplasm that is obtained at different moments in time during treatment of the neoplasm (e.g. with medication or chemo-radiation), can be combined to provide a predictive value that allows to assess the effectiveness of treatment. This predictive value can thus be utilized by a physician to support decisions taken during treatment, e.g. a decision to modify the medication administered, the frequency of administration, the dose, or a modification in the radiation treatment (e.g. frequency, dose, combination with chemo). Obtaining and combining these image features from the imaging data allows to provide such a predictive value at an early stage during treatment. This is advantageous because timely information on treatment effectiveness can increase the success rate of treatment.

In accordance with the present invention, a prediction model contains information on which image features are to be combined in what manner. The term 'prediction model' is to be understood as a data set containing indications of the particular image features that are to be combined and their associated multiplier values. The multiplier values may enable correctly weighing of the respective image features in the combination that yields the predictive value. The term 'image feature' is to be understood as a characteristic feature of the imaged neoplasm. For example an image of a tumor may show the tumor to be of a more or less even colour and intensity; which may be expressed in the image features relating to heterogeneity of the tumor. An image feature may be quantitatively described by image feature parameters, which image feature parameters have a specific image feature parameter value in an image of the examined tumor.

During treatment, if the treatment is effective, the image feature parameter value of some specific image features may have been changed in a second image taken from the tumor, as compared to a first image taken at an earlier moment. As may be appreciated, if treatment is not effective, the particular image features may also change or not change at all. However, the image feature parameter value may then change in a different manner. Therefore, a combination of carefully selected image features can be indicative of treatment effectiveness. The present invention uses a prediction model that indicated and weighs, by means of multiplier values, which image features are to be combined. For each image feature to be combined, it then multiplies the respective image feature difference value, i.e. a parameter that directly quantifies the difference of a respective image feature parameter, with the associated multiplier value for that image feature as included as data in the prediction model. The present invention allows to include one or more image feature difference values, but also one or more of the original image features from different time points. Taking the difference of image feature parameters may be performed before or after multiplication with a multiplier value.

In accordance with an embodiment, additionally, one or more image feature parameter values from a specific time point can be included in the prediction model (with or without an associated weighing factor or multiplier value), to calculate the predictive value.

The combination of these weighed (i.e. multiplied by the multiplier value) image feature difference values may be performed in different manners to yield a useable predictive value. For example, the weighed image feature difference values may be combined by simply adding them up, or using a polynomial. Also, a logarithmic function may be used for combining the weighed image feature difference values. Most importantly, the image features to be included are carefully selected and their contribution is correctly weighed by means of the multiplier values. To this end, the prediction model (obtained from a memory of a decision support system) comprises the one or more multiplier values associated with the image features.

The fundamental hypothesis underlying the invention is that quantitative image feature analysis better allows therapies to be tailored to individual patients and thus lead to improved survival and quality of life. Therefore the present image analysis method and system enables to compare imaging data available through conventional clinical imaging tools (CT, PET/CT, MR and MR/PET) to combine into a predictive value using a prediction model allowing to establish early information on the effectiveness of treatment to the aid of a medical practitioner. The invention converts imaging data, by using a high number of automatically extractable image metrics, into a high dimensional mineable feature space (i.e. "radiomics"). From this, the image feature difference values may be obtained and combined (i.e. "delta radiomics") using the prediction model to provide the predictive value.

The particular image features that are used in and make up the various prediction models that may be used in the method in accordance with the present invention, will be explained in more detail later in this document. These image features have in common that each of them is derivable by performing advanced image analysis of the image data. Moreover, these features are reproducible. For example a part of the image features used in the prediction models relate to tumor intensity, and may be derived from the intensity or color of individual pixels or areas within the image, or from (statistical) analysis of the image histogram. As a further example, part of the image features relate to the shape and size of a tumor, and may be derived amongst others from contour analysis. Moreover, a further part of the image features describes textural differences of the image of the tumor, and may for example be determined using a co-occurrence matrix of the image. These latter features may for example relate to homogeneity and heterogeneity differences in the texture. Other image features may be derived from an intensity volume histogram obtainable from positron emission tomography (PET) images, i.e. a histogram of volume intensity values within the tumor or neoplasm.

In accordance with an embodiment of the invention, the multiplier values include one ore more weighing factors associated with the image features, wherein the weighing factors indicate an importance of the respective image features for obtaining the predictive value. Moreover, in accordance with yet another embodiment, the multiplier values include one or more selector values associated with the image features, wherein the selector values indicate whether the associated image features are to be included for obtaining the predictive value. The multiplier values may include either one or both of weighing factors or selector values.

In accordance with another embodiment, the step of calculating an image feature difference value comprises calculating an image feature difference percentage. Although in some embodiments, the absolute image feature parameter difference value may be applied, in other embodiments the predictive value is calculated using the relative difference or difference percentage instead of the absolute difference.

The image data may be obtained using a variety of imaging methods. For example, the image data may obtained using at least one of a group comprising a computed tomography imaging method (single, dual or multiple energy), a positron emission tomography method (fluorodeoxy glucose or other biomarkers, such as (but not limited to) Fmiso, HX4 . . . ), a magnetic resonance imaging method (for example (but not limited to) magnetic fields of 1.5 to 9 Tesla), a single photon emission computed tomography imaging method, a planar gamma imaging method, an ultrasonography imaging method, a thermography imaging method, or a photo-acoustic imaging method.

In the image analysis method in accordance with the embodiments of the present invention, the image feature parameters may further include at least one of a group comprising first-order gray level statistics obtained from image pixels or area's of the image from the image data, such as energy, mean absolute deviation, root mean square, uniformity, minimum intensity, maximum intensity, mean intensity, median, intensity range, intensity variance, intensity standard deviation, skewness, kurtosis, variance and entropy; second-order gray level statistics obtained from co-occurrence matrices of the image data, such as contrast, correlation between neighboring image areas or pixels, energy, homogeneity first type, homogeneity second type, inverse difference moment, sum average, sum variance, sum entropy, autocorrelation, cluster prominence, cluster shade, cluster tendency, dissimilarity, normalized inverse difference moment, normalized inverse difference, inverse variance; run-length gray level statistics, short run emphasis, long run emphasis, run percentage, gray-level non-uniformity, run length non-uniformity, low gray level run emphasis, high gray level run emphasis; shape and size based features, such as perimeter, cross-sectional area, major axis length, maximum diameter, and volume; gray-level size-zone matrix based features, such as small area emphasis, large area emphasis, intensity variability, size-zone variability, zone percentage, low intensity emphasis, high intensity emphasis, low intensity small area emphasis, high intensity small area emphasis, low intensity large area emphasis, or high intensity large area emphasis; or intensity volume histogram based features of positron emission tomography images.

In accordance with the present invention, a number of particular image feature combinations (hence prediction models) have been identified as providing a well and useful prediction value for non small cell lung cancer (NSCLC) In particular two image feature combinations (prediction models) were identified based on image data obtained from computed tomography (CT) images, and two image feature combinations (prediction models) were identified based on image data obtained from positron emission tomography (PET) images. The embodiments relating to these combinations are provided below. Detailed explanations of image feature parameters, including descriptive algorithms, are included later on in this document. Some of the parameters described are first pre-processed by performing a transform on the image data or the parameter. For example, some parameters are included in the combination by first performing a wavelet transform which effectively decouples textural information by decomposing the original image, in a similar manner as Fourier analysis, in low- and high-frequencies. Moreover, the multiplier values included in the prediction models are herein below expressed in terms of a parameter termed 'hazard ratio' (or abbreviated: HR (e.g. in algorithms)).

In accordance with some embodiments, the image data is obtained using a computed tomography imaging method, wherein the first and second image feature parameter values are quantitative values obtained from said first and second image data and associated with image feature parameters, the image feature parameters including at least: a high-high-low filtered wavelet transform (abbreviated: wavelet HHL) of the parameter kurtosis from the class first level statistics; a high-low-low filtered wavelet transform (abbreviated: wavelet HLL) of the parameter homogeneity second type (abbreviated: 'homogeneity 2') from the class second order gray-level statistics.

In specific embodiments wherein the above combinations are applied, the prediction model may include the following multiplier values as indicated in table 1 below.

TABLE 1

| Feature | HR | HR range |
|---|---|---|
| Wavelet HHL kurtosis (class: statistics) | 0.99 | 0.980 to 0.995 |
| Wavelet HLL homogeneity 2 (class: GLCM) | 1.01 | 1.005 to 1.020 |

In accordance with some embodiments, the image data is obtained using a computed tomography imaging method, and the first and second image feature parameter values are quantitative values obtained from said first and second image data and associated with image feature parameters, the image feature parameters including at least: the parameter run-length non-uniformity from the class run-length gray-level statistics (RLGL); the parameter uniformity from the class first order statistics (abbreviated: statistics); a high-low-high filtered wavelet transform (abbreviated: wavelet HLH) of the parameter normalized inverse difference moment from the class second order gray-level statistics (gray level co-occurrence matrix; abbreviated: GLCM).

In specific embodiments wherein the above combinations are applied, the prediction model may include the following multiplier values as indicated in table 2 below.

TABLE 2

| Feature | HR | HR range |
|---|---|---|
| Run-length non-uniformity (class: RLGL) | 1.06 | 1.01 to 1.10 |
| Uniformity (class: statistics) | 1.01 | 1.01 to 1.02 |
| Wavelet HLH normalized inverse difference moment (class: GLCM) | 2.12 | 1.09 to 4.10 |

In accordance with some embodiments, the image data is obtained using a positron emission tomography imaging method, wherein the first and second image feature parameter values are quantitative values obtained from said first and second image data and associated with image feature parameters, the image feature parameters including at least: the parameter entropy from the class first level statistics; the parameter root mean square from the class first level statistics.

In specific embodiments wherein the above combinations are applied, the prediction model may include the following multiplier values as indicated in table 3 below.

TABLE 3

| Feature | HR | HR range |
|---|---|---|
| Entropy (class: statistics) | 0.95 | 0.90 to 1.00 |
| Root mean square (class: statistics) | 1.03 | 1.01 to 1.05 |

In accordance with some embodiments, the image data is obtained using a positron emission tomography imaging method, and wherein the first and second image feature parameter values are quantitative values obtained from said first and second image data and associated with image feature parameters, the image feature parameters including at least: the parameter absolute intensity of a part of a volume (absolute intensity of relative volume; abbreviated: $AIRV_x$) of the neoplasm determined using an intensity volume histogram (abbreviated: IVH) of said image data, such as an absolute intensity of a relative volume of 30% of highest intensity (abbreviated: $AIRV_{30\%}$); the parameter total lesion glycolysis for a volume of the neoplasm having an absolute intensity above a threshold (abbreviated: $TLGAI_y$) determined using an intensity volume histogram (IVH) of said image data, such as a total lesion glycolysis for a volume of the neoplasm having an absolute intensity above 3.0 (abbreviated: $TLGAI_{3.0}$); the parameter uniformity from the class first order statistics.

In specific embodiments wherein the above combinations are applied, the prediction model may include the following multiplier values as indicated in table 4 below.

TABLE 4

| Feature | HR | HR range |
|---|---|---|
| $AIRV_{x\%}$ (class: IVH) (e.g. $AIRV_{30\%}$) | 1.03 | 1.01 to 1.05 |
| $TLGAI_y$ (class: IVH) (e.g. $TLGAI_{3.0}$) | 0.99 | 0.97 to 1.01 |
| Uniformity (class: statistics) | 1.01 | 0.99 to 1.03 |

In accordance with a further aspect of the present invention there is provided a decision support system for performing an image analysis method in accordance with a first aspect described hereinabove for providing information for supporting illness development prediction regarding a neoplasm in a human or animal body, the system comprising a processing unit, and further comprises: an input communicatively connected to the processing unit for receiving, by the processing unit, image data of the neoplasm, wherein said receiving comprises the steps of receiving first image data of the neoplasm at a first moment in time and receiving second image data of the neoplasm at a second moment in time; the processing unit further being arranged for deriving for each of a plurality of image features associated with the neoplasm, a first image feature parameter value from the first image data and a second image feature parameter value from the second image data, said first and second image feature parameter value being a quantitative representation of said respective image feature at said first and second moment in time respectively; and the processing unit being arranged for calculating for each of the plurality of image features, an image feature difference value by calculating a difference between the first and second image feature parameter value for said respective image feature; wherein the processing unit is further arranged for deriving, using a prediction model obtained from a memory of the decision support system, a predictive value associated with the neoplasm for supporting treatment thereof, wherein said prediction model includes a plurality of multiplier values, each multiplier value being associated with an image feature for multiplying an associated image feature difference value therewith, wherein for calculating the predictive value the processing unit is arranged for multiplying each image feature difference value with its associated multiplier value and combining the multiplied image feature difference values such as to obtain the predictive value for the neoplasm.

The invention, in accordance with further aspects thereof, relates to a computer program product, wherein the computer program product comprises computer instructions which, when run on a computer, are arranged for performing an image analysis method in accordance with the first aspect; and to a transitory or non-transitory computer readable medium comprising such a computer program product.

BRIEF DESCRIPTION OF THE DRAWINGS

The present invention will further be elucidated by means of some specific embodiments thereof, with reference to the enclosed drawings, wherein:

FIG. 1A-2 is a histogram of the image of FIG. 1A-1;

FIG. 1A-3 provides an overview of image feature parameter values and corresponding image feature parameters derived from first order gray level statistics of the gray level image of FIG. 1A-1;

FIG. 1B-1 provides a gray level image describing tumor intensity of a second tumor;

FIG. 1B-2 is a histogram of the gray level image of FIG. 1B-1;

FIG. 1B-3 provides an overview of image feature parameter values and associated image feature parameters derived from first order gray level statistics obtained by analyzing the image of FIG. 1B-1;

FIG. 2A-1 illustrates a three dimensional representation of a third tumor;

FIG. 2A-2 provides an overview of image feature parameter values of image feature parameters obtained from shape and/or size analysis of the tumor based on FIG. 2A-1;

FIG. 2B-1 provides a three dimensional representation of a fourth tumor;

FIG. 2B-2 provides an overview of image feature parameter values and associated image feature parameters obtained by shape and/or size analysis based on the image illustrated in FIG. 2B-1;

FIG. 3 is an illustration of a surface contour analysis for obtaining the maximum diameter of a tumor;

FIG. 5 is a schematic illustration of a decision support system in accordance with an embodiment of the present invention;

FIG. 8 is a gray scale ROI image of a tumor from which a gray-level co-occurrence matrix may be determined in accordance with an embodiment of the invention;

DETAILED DESCRIPTION

Figures 1, 1A:
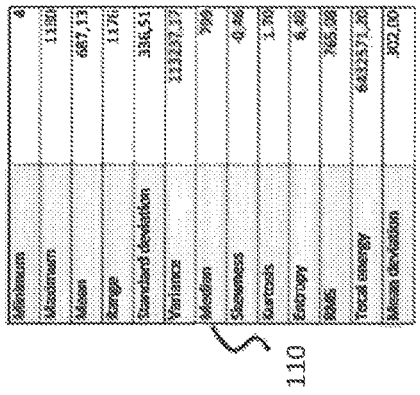
FIG. 1A-1 is a gray level image describing tumor intensity of a first tumor.

Before providing a more detailed description of the various image feature parameters which may be derived from image features obtained from imaging data of neoplasms such as tumors, a description will be given herein below with reference to FIGS. 5 and 6 of a decision support system and an image analysis method in accordance with the present invention.

FIG. 5 schematically illustrates a decision support system in accordance with an embodiment of the present invention. In FIG. 5, the decision support system 1 comprises at least an analysis unit 3 which is connected to an imaging system 8. The imaging system 8 may be any suitable imaging system used in medical environments for diagnostic purposes, in particular for visualizing tumors. The imaging system 8 may for example be a magnetic resonance imaging system (MRI), a computer tomography system (CT), a positron emission tomography system (PET), a single photon emission computer tomography system (SPECT), an ultrasonography system, a tomography system, or a photo acoustic imaging system. The imaging system 8 may provide image data directly to the analysis system 3, or may alternatively store the image data in a data repository data system 10 from which it may be obtained by the analysis system 3 at any time required. As will be appreciated, the analysis system 3, the imaging system 8, the data repository system 10, and any output terminal or system 12, may be connected with each other via a data network, or via direct data connections.

As mentioned hereinabove, the analysis system 3 receives imaging data either directly from the imaging system 8 or retrieves it from a data repository system 10 where the image data may be stored. Another possibility is that part of the image data is received directly from the imaging system 8 by analysis unit 3, and another part of imaging data, e.g. imaging data taken from a same tumor at an earlier stage during a treatment of a patient, may be obtained from data repository system 10. As will be appreciated, imaging data may alternatively be obtained from another source or via other means. For example, such data may be obtained from a remote network, from an e-mail server, or from a data storage entity such as a memory stick or an SD card. Performing an analysis in accordance with the present invention on imaging data taken at various stages throughout a treatment process provides information to a medical practitioner that may be used for evaluating the treatment process, and to take necessary action.

The analysis unit 3 comprises a processing unit which receives the image data from input/output ports 6 and 7. The processing unit is arranged for deriving a plurality of image feature parameter values of image feature parameters associated with image features from the image data received. An image feature parameter is a quantitative representation of the associated image feature, and the image feature parameter value is the value of that respective parameter for the respective image data considered. For said deriving, the processing unit 4 applies various analysis algorithms, such as statistical analysis algorithms, graphic analysis algorithms and the like. Such algorithms may for example be stored in memory unit 5 within analysis unit 3. The processing unit may further be arranged to obtain one or more prediction models from memory unit 5. Each of the obtained prediction models comprises selector values which determine whether or not, and to what extend or with what weight specific image feature parameters are to be included in the respective prediction model. The prediction models may comprise either one or both of said selector values and weighting factors separately or integrated in a single multiplier value, as stored in memory unit 5. Such weighting factors not only determine that a certain image feature parameter is included in the prediction model, but also enable to prescribe the importance of a certain image feature parameter in the prediction model, e.g. in terms of its predictive value in relation to or in combination with other parameters.

The processing unit 4 is arranged for receiving image data of the neoplasm via input 6 or 7. This receiving step comprises receiving first image data of the neoplasm taken at a first moment in time, and receiving second image data of the neoplasm taken at a second moment in time. From this first and second image data, the processing unit derives for each of a plurality of image features associated with the neoplasm, image feature parameter values. Thus a first image feature parameter value from the first image data is derived, and a second image feature parameter value from the second image data is derived by the processing unit. These first and second image feature parameter values are quantitative representations of the respective image feature considered, at said first and second moment in time respectively.

From the first and second image feature parameter values now available, the processing unit calculates for each of the plurality of image features, an image feature difference value. This may be performed by calculating a difference between the first and second image feature parameter value for said respective image feature. Alternatively, in accordance with an embodiment, the processing unit calculates a relative image feature difference value or percentage value, instead of or in addition to the absolute difference value. For example, the following formula may be used:

$$\frac{(IFP_2 - IFP_1)}{IFP_1} \times 100\% = \Delta IFP_\%$$

wherein, $IFP_1$ and $IFP_2$ are respectively the first and second image feature parameter value, and $\Delta IFP\ \%$ is the relative image feature difference value or percentage value.

Using a prediction model obtained from memory 5 (although it could equally be obtained from an external repository such as data repository system 10), the processing unit derives a predictive value associated with the neoplasm for supporting treatment thereof. The predictive value provides an indication of whether or not, and to what extend, treatment of the tumor or neoplasm is effective. If it is not effective, there may be no or insufficient difference between the first and second image feature parameter values considered; or alternatively such image feature parameter values could indicate a progression of the illness in the undesired direction (e.g. growth of the tumor). If, however, the treatment is effective, the combined image feature difference values will indicate a change in a desired direction. The image features considered, as indicated by the prediction model obtained from memory 5, are suitably selected and multiplied with their weighing factors such as to be early indicators for such successful or unsuccessful treatment.

To this end, the prediction model includes a plurality of multiplier values, each multiplier value being associated with an image feature for multiplying an associated image feature difference value therewith. For calculating the predictive value the processing unit 4 multiplies each image feature difference value with its associated multiplier value and combines the multiplied image feature difference values such as to obtain the predictive value for the neoplasm. Such combination may be via any suitable algorithm, e.g. a mere summing, a polynomial or a logarithmic or exponential algorithm.

Figure 6:
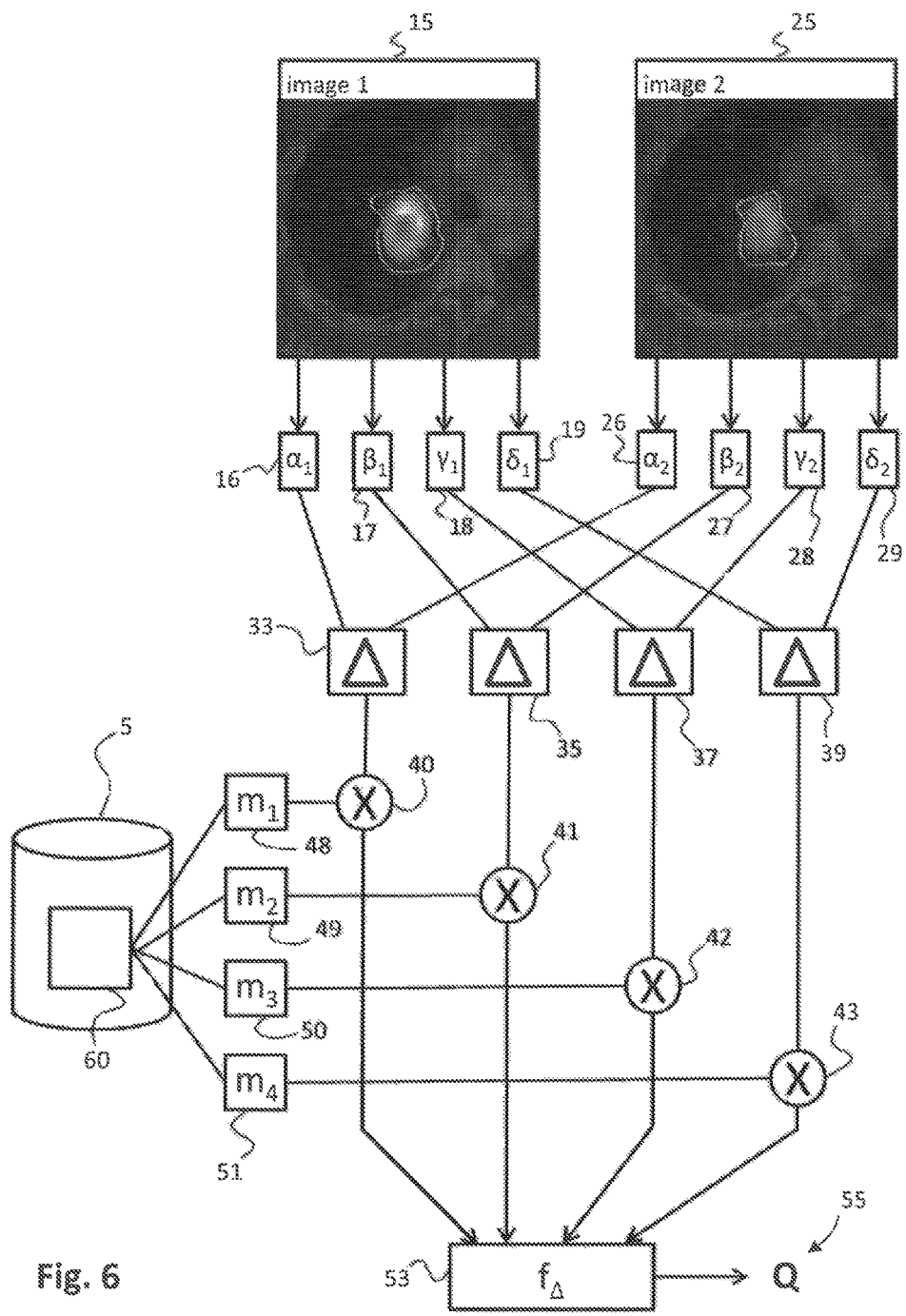
FIG. 6 is a schematic illustration of an embodiment of an image analysis method of the present invention.
Figure 7:
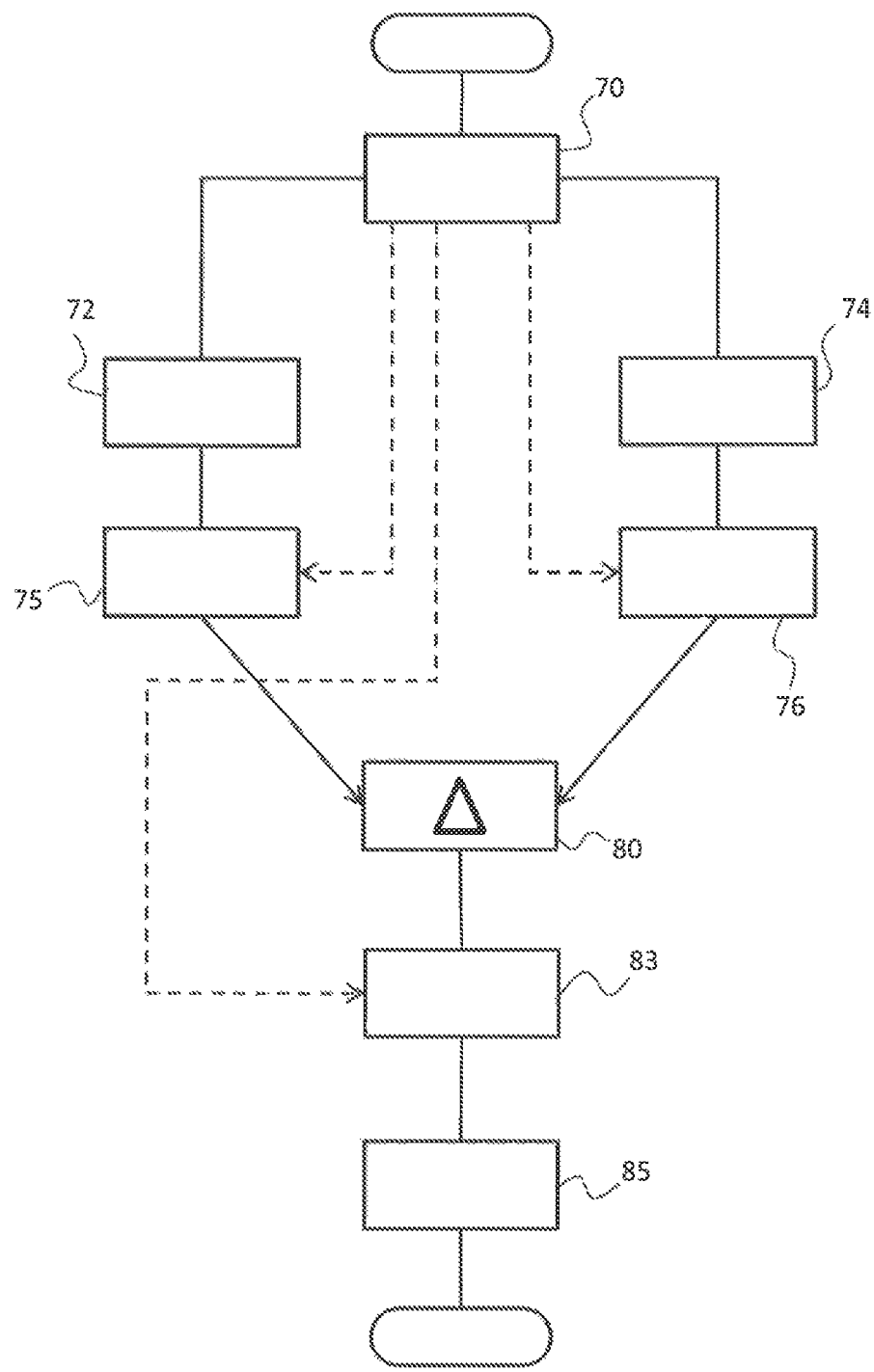
FIG. 7 is a further schematic illustration of a method of the present invention.

In FIGS. 6 and 7, embodiments of analysis methods in accordance with the present invention are schematically illustrated. FIG. 6 schematically illustrates the data processing performed in a method of the present invention. FIG. 7 illustrates an image analysis method of the present invention as it may be implemented in terms of steps performed by hardware or software elements of a decision support system in accordance with the invention. To explain the method in relation to a decision support system of the invention, reference is also made to the reference numerals and features of FIGS. 5, 6 and 7. As will be appreciated, the method and the system are only provided as an example and should not be interpreted limiting. The order of the steps illustrated in FIG. 7 may be different such as to enable performing data processing in accordance with FIG. 6. Also, additional or alternative steps may be implemented without departing from the teachings of the present invention. Some steps may be dispensed with in case they may be implemented in an alternative manner, without departing from the present invention.

In FIG. 7, in step 70 a prediction model 60 (as illustrated in FIG. 6) may be retrieved from a memory 5 of the analysis unit 3 (or from an external memory 10, as illustrated in FIG. 5). Then, in step 72, first image data of a tumor (or other neoplasm) is received by the processing unit 4. For example, this first image data may be image data 15 illustrated in FIG. 6. Likewise, in step 74, second image data of the same tumor is received by the processing unit 4. This second image data may be image data 25 illustrated in FIG. 6, and comprises image data of the same tumor as in image data 15 but taken at a later moment in time. For example, the first image data 15 may have been obtained prior to treatment, e.g. on the day the that the treatment started, while second image data 25 may have been obtained after n days of treatment (wherein n indicates the number of days), e.g. after 15 days. The first and second image data may be received in steps 72 and 74 from a memory (e.g. memory 5 or data repository 10) or may be received directly from an imaging system (e.g. imaging system 8). Moreover, step 70, which is in FIG. 7 illustrated prior to steps 72 and 74, may be performed after receiving the image data in steps 72 and 74, and even after the subsequent steps 75 and 76.

In step 75, a number of first image feature parameters, such as first image feature parameters 16, 17, 18 and 19 in FIG. 6, are derived from the first image 15. The decision on which first image feature parameters 16-19 are to be derived may be based on information obtained from the prediction model 60 received in step 70; but alternatively it is also possible that the processing unit 4 calculates all possible image feature parameters of the first image data 15 and stores them for later selection. Likewise, in step 76, the second image feature parameter values 26, 27, 28 and 29 are derived from the second image data 25. As will be appreciated, the second image feature parameters 26-29 relate to the same image feature parameters $\alpha$, $\beta$, $\gamma$, and $\delta$ as the first image feature parameters 16-19 that were taken from the first image data 15.

In step 80 of FIG. 7, the image feature difference values 33, 35, 37, and 39 as illustrated in FIG. 6 are calculated by the processing unit 4. These difference values 33, 35, 37, and 39 may be real or absolute difference values (e.g. for image feature parameter $\alpha$, this could be: $\Delta\alpha = \alpha_2 - \alpha_1$; thus based on parameter values 16 and 26). Alternatively, a percentage difference may be used (e.g. for parameter $\alpha$, this could be: $\Delta\alpha = 100\% * ((\alpha_2 - \alpha_1)/\alpha_1)$; thus based on parameter values 16 and 26). Although in some embodiments, the decision to use percentage differences or real or absolute differences may be predetermined (e.g. processing all parameters in the same manner in this respect), in other embodiments the prediction model 60 may indicate whether for a certain image feature parameter, either the real, absolute or percentage difference may have to be used. Whichever implementation is used, step 80 of FIG. 7 provides the image feature difference values, e.g. values 33, 35, 37, and 39 indicated in FIG. 6.

In step 83 of FIG. 7, the processing unit 4 retrieves the relevant multiplier values from the prediction model; e.g. these may be multiplier values $m_1$-$m_4$ (elements 48, 49, 50, and 51) from prediction model 60 in memory 5 as illustrated in FIG. 6. Also in step 83, these multiplier values 48-50 are multiplied with the image feature difference values 33, 35, 37, and 39 of their associated image features. This yields the weighed image feature difference values 40, 41, 42, and 43 illustrated in FIG. 6.

In the optional implementation suggested above, wherein in steps 75 and 76 the processing units has calculated all image feature parameter values without first consulting the prediction model 60 on which image features to include, the associated difference values of all these parameters would have been calculated and stored in step 80, and step 83 would multiply these difference values with their multiplier values. In that case, the multiplier values $m_1$-$m_4$ (e.g. 48-51) could both act as weighing factors as well as selector values by being equal to '0' in case the image feature difference value is not to be included, while being equal to the real weighing factor in case the image feature difference value is to be included.

In step 85 of FIG. 7, the weighed image feature difference values are combined such as to yield the predictive value (e.g. predictive value Q (element 55) in FIG. 6) that is the outcome of the method. For example, as illustrated in FIG. 6, combination (element 53) could include the calculation of the predictive value using function $f_A$. However, the function $f_A$ could be a summing of the values 40-43 in FIG. 6. After step 85, the method may end.

As will be appreciated, the decision support system of FIG. 5 and the image analysis method of FIGS. 6 and 7 are embodiments of the present invention, however the invention may be practice otherwise then specifically described with reference to FIGS. 5, 6 and 7. For example, additional image feature parameter values from either one or both of the first image data 15 and second image data 25, or even from third image data of an image taken at another point in time, may be included for calculating the predictive value. Such additional image feature parameter values thus not necessarily are to be included by their difference values with respect to a second image, although this is of course not prohibited.

The present invention uses image feature parameter values obtained from image features derived from image data of a tumor. FIGS. 1A-1 through 1B-3 provide as a first example a number of image feature parameters and their values that may be obtained from first order gray level statistical analysis of an image. In FIG. 1A-1, a gray level image of a tumor is illustrated. The gray level scale is indicated with reference numeral 103 to the right of FIG. 1A-1. Also visible in FIG. 1A-1 is the contour 101 of the tumor to be analyzed. It is to be noted that the contour defining the tumor will usually be determined by a medical practitioner, or any other analysis method or system. The present description assumes this information to be available to the method.

Figures 1, 1A, 2:
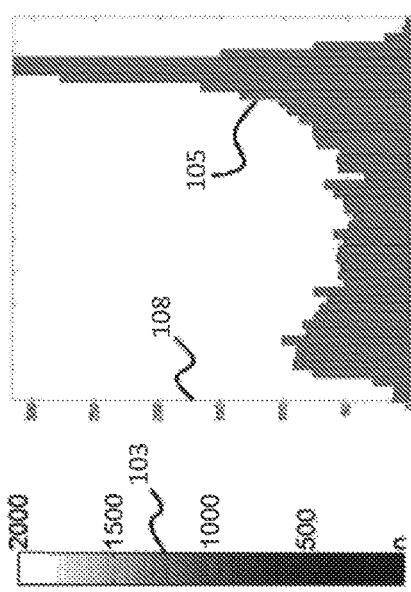

In FIG. 1A-2 a histogram 105 is illustrated which is based on the image data illustrated in FIG. 1A-1. The histogram 105 resembles the tumor image only, i.e. the histogram is based on the pixels of the gray level image FIG. 1A-1 inside the contour 101. All parts of the image outside contour 101 are disregarded from the analysis and is considered to be healthy tissue. The histogram 105 is plotted onto a first access 107 indicating the gray level considered, and a second access 108 resembling the number of pixels occurring with gray level.

Figures 1, 1A, 2, 3:
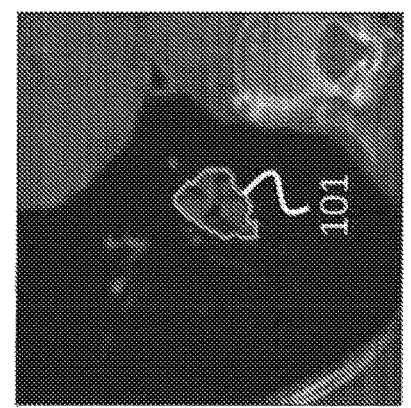
Figures 1, 1B:
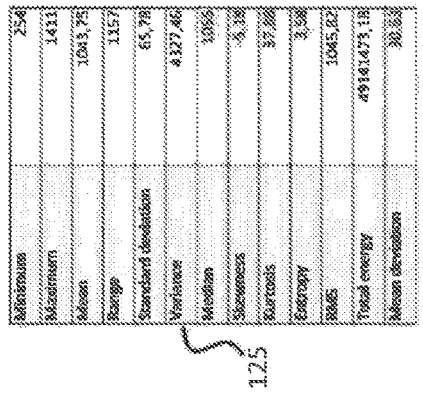
Figures 1, 1B, 2:
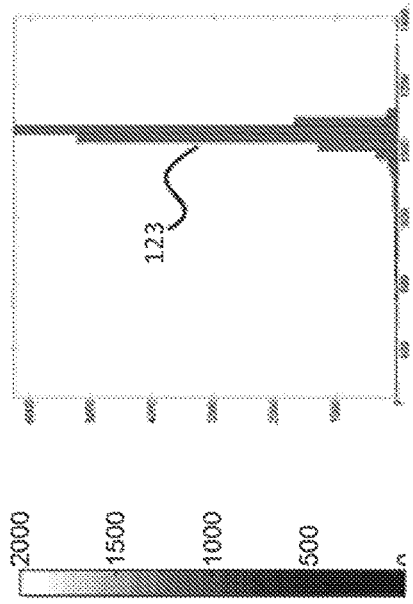
Figures 1, 1B, 2, 3:
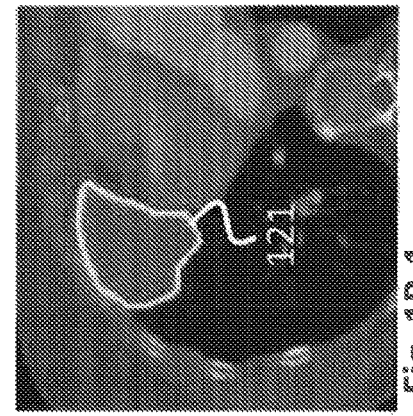

FIG. 1B-1 illustrates a second tumor within contour 121, and FIG. 1B-2 illustrates a corresponding histogram 123 associated with this second tumor illustrated in FIG. 1B-1. From a qualitative comparison of the images of FIG. 1A-1 and FIG. 1B-1, one can see a number of characteristic differences between the two tumors. For example, the first tumor within contour 101 appears to be inhomogeneous, while the gray level of the second tumor 121 is more uniform. This difference is for example directly visible in the histograms 105 and 123. Histogram 123 is clearly concentrated around a uniform gray level as a small but sharp peak. Histogram 105 illustrates a broad distribution having a peak at approximately gray level 1050 and a more distributed trail across almost all gray levels below this value. From the histogram of the image of the tumor, relevant information can be quantitatively derived that may also be derived from qualitative examination of the images.

In FIGS. 1A-3 and FIG. 1B-3, an overview is provided from a number of image feature parameter values and associated image feature parameters that may be derived from first order gray level statistical analysis of the images of FIGS. 1A-1 and 1B-1 respectively. These image feature parameters, which will be described with more detail later on in this document, may be used in the various prediction models to obtain a predictive value, which may be supportive to the medical practitioner in early assessment of treatment effectiveness.

FIGS. 2A-1 through 2B-2 provide an example of image feature parameter and image feature parameter values that may be obtained from analysis of shape and size related features, derivable for example from three dimensional (3D) representations of tumors based on imaging data obtained. In FIG. 2A-1 a three dimensional (3D) representation of a third tumor 130 is illustrated. In FIG. 2B-1 a three dimensional (3D) representation of a fourth tumor 135 is illustrated. From qualitative comparison of the two tumors in FIGS. 2A-1 and FIGS. 2B-1, a number of differences may be derived such as a difference in size of the tumor. The fourth tumor 135 is much larger than the third tumor 130, although the third tumor 130 appears to have a much larger surface.

An overview of the image feature parameter values that may be derived from the imaging data in FIGS. 2A-1 and FIG. 2B-1 is provided in FIGS. 2A-2 and 2B-2 respectively. These image feature parameter values for example include the volumes of the tumors, their total surface and their maximum diameter. Besides this, more quantitative information on image feature parameters which may be characteristic for a specific type of tumor growth (phenotype) is derivable from the images. For example, the sphericity provides information on how spherical (i.e. regular) the tumor is. The surface to volume ratio (SVR) expresses how spiky or sharp the tumor is. A maximum diameter represents the maximum distance between the most remote points on the surface of the tumor in the three dimensional representation.

FIG. 3 provides an illustration of a contour analysis from which the maximum diameter of a tumor may be derived. The most remote points in FIG. 3 are at the ultimate ends of the tumor 140, to the left and right side of the plot in FIG. 3. In respect of FIG. 3 it is noted that the points depicted in the plot are voxels lying on the surface of the tumor.

Figure 4A:
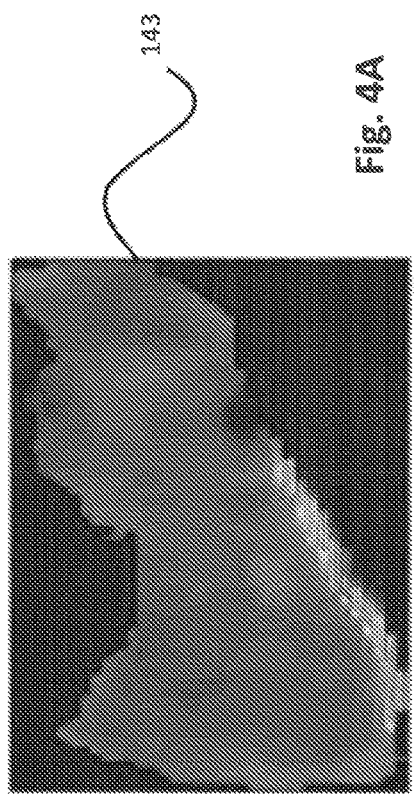
FIG. 4A provides an image of a fifth tumor.
Figure 4B:
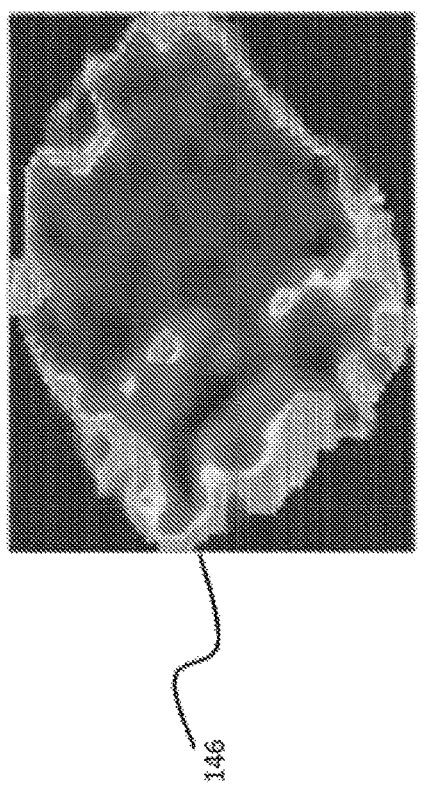
FIG. 4B provides an image of a sixth tumor.

As a further example in FIGS. 4a and 4b, a fifth tumor 143 and a sixth tumor 146 are respectively illustrated. From qualitative observation of the images in FIG. 4a and FIG. 4b, a striking difference is visible in terms of the texture of the tumors illustrated. For example, the sixth tumor 146 in FIG. 4b illustrates a strong variation in color inside the tumor and across its surface. The tumor 143 in FIG. 4a is more homogeneous, being more or less of one color. These differences in texture can be derived from co-occurrence matrices obtained from pixel color analysis of the images of these figures. The concept of co-occurrence matrices will be explained later.

Image Feature Parameter Descriptions (Part 1)

In this section 'image feature parameter descriptions (part 1)', a large number of image feature parameters are described which can be obtained from the image data received. The image feature parameters relate to different classes of parameters, wherein each class of parameters is somewhat similar in terms of the manner in which the parameters are obtained. For example, for some classes, a certain preprocessing step is to be performed by a processing unit 4 on an analysis unit 3, in order to calculate each parameter. This preprocessing is similar for all parameters in that class, for example as is the case for the second order gray-level statistics. Other classes may relate to a certain type of parameters, e.g. first order gray-level statistics includes statistical parameters obtainable directly from the image data. Further image feature parameter descriptions for these and other classes may be found in section 'image feature parameter descriptions (part 2)' later on.

First-Order Gray Level Statistics

In this section various image feature parameters are described that can be used to extract and summarize meaningful and reliable information from CT images. We will describe the extraction of image traits that may be used to derive prognostic metrics, and that may be incorporated into prediction models of a decision support system, to beneficially support the clinical review process of a treatment, and to modify a patient's treatment in case of predicted ineffectiveness of a present treatment. As appreciated, the objective of the invention is to support (not take over) the decision making process of the medical practitioner with advanced information taken from the images; i.e. image feature data that cannot be objectively assessed by means of qualitative interpretation.

We explore first-order statistics of the image histogram through the commonly used metrics. We denote by I(x,y) as the intensity or gray-level values of the two-dimensional pixel matrix. Note that this notation I(x,y) assumes a two dimensional image. However, the invention may well apply corresponding image feature parameters of three-dimensional images, in which case the intensity matrix may be denoted as I(x,y,z) or I(X) where X=X(x,y,z) (or with different coordinates if not Cartesian). Summing may in that case be correspondingly performed over all values, hence in three coordinates. The formulas used for the first order statistics are as follows:

1. Minimum $$I_{min} = \min\{I(x,y)\} \tag{B.1}$$

2. Maximum $$I_{max} = \max\{I(x,y)\} \tag{B.2}$$

3. Range $$R = \max\{I(x,y)\} - \min\{I(x,y)\} \tag{B.3}$$

4. Mean $$\mu = \frac{1}{XY} \sum_{x=1}^{X} \sum_{y=1}^{Y} I(x, y) \tag{B.4}$$

5. Variance $$\sigma^2 = \frac{1}{(XY-1)} \sum_{x=1}^{X} \sum_{y=1}^{Y} [I(x, y) - \mu]^2 \tag{B.5}$$

6. Standard Deviation $$s = \left(\frac{1}{XY-1} \sum_{i=1}^{XY} (x_i - \mu)^2\right)^{1/2} \tag{B.6}$$

7. Skewness $$\frac{1}{XY}\sum_{x=1}^{X}\sum_{y=1}^{Y}\left[\frac{I(x,y)-\mu}{\sigma}\right]^{3} \quad (B.7)$$

8. Kurtosis $$\frac{1}{XY}\sum_{x=1}^{X}\sum_{y=1}^{Y}\left\{\left[\frac{I(x,y)-\mu}{\sigma}\right]^{4}\right\}-3 \quad (B.8)$$

9. Entropy $$H = -\sum_{i=1}^{XY} P(i) \cdot \log_2 P(i) \quad (B.9)$$

In B.9 P(i) is the first order histogram, that is, P(i) is the fraction of pixels with gray level i. The variance ($\mu_2$), skewness ($\mu_3$) and kurtosis ($\mu_4$) are the most frequently used central moments. The variance is a measure of the histogram width, that is, a measure of how much the gray levels differ from the mean. The skewness measures the degree of histogram asymmetry around the mean, and kurtosis is a measure of the histogram sharpness. As a measure of histogram uniformity or randomness we computed the entropy of the image histogram. The closer to a uniform distribution the higher the entropy, or seen in a different way, H would take low values in smooth images where the pixels have the same intensity level.

Second-Order Gray Levels Statistics

The features shown above that resulted from the first-order statistics provide information related to the gray-level distribution of the image; however they do not provide any information regarding the relative position of the various gray levels over the image. This information can be extracted from the so called co-occurrence matrices where pixels are considered in pairs and which provide a spatial distribution of the gray level values. The co-occurrence features are based on the second-order joint conditional probability function P(i,j;a,d) of a given image. The ith, jth element of the co-occurrence matrix for a given tumor image represents the number of times that the intensity levels i and j occur in two pixels separated by a distance (d) in the direction ($\alpha$). The co-occurrence matrix for a pair (d,a) is defined as the $N_g \times N_g$ matrix where $N_g$ is the number of intensity levels. The $N_g$ levels were obtained by scaling the gray-level image to a discrete $N_g$ number of gray-level values. The $N_g$ values are normally selected in powers of 2; here we have selected 32 discrete gray-level values which in practice is a sufficient choice for representing the image. Here d was set to a single pixel size and a covered the four available angular directions (horizontal, vertical, diagonal and anti-diagonal). Let for example an image array I(x,y) be:

$$I = \begin{bmatrix} 3 & 5 & 8 & 10 & 8 \\ 7 & 10 & 3 & 5 & 3 \\ 7 & 3 & 5 & 1 & 8 \\ 2 & 6 & 7 & 1 & 2 \\ 1 & 2 & 9 & 3 & 9 \end{bmatrix} \quad (B.11)$$

which corresponds to a 5×5 image. We can assume the number of discrete gray levels is equal to 10. Thus for the image (B.11) and a relative pixel position (1.0°) we obtain:

$$GLCM^0(d=1) = \begin{bmatrix} 0 & 2 & 0 & 0 & 0 & 0 & 0 & 1 & 0 & 0 \\ 0 & 0 & 0 & 0 & 0 & 1 & 0 & 0 & 1 & 0 \\ 0 & 0 & 0 & 0 & 3 & 0 & 0 & 0 & 1 & 0 \\ 0 & 0 & 0 & 0 & 0 & 0 & 0 & 0 & 0 & 0 \\ 1 & 0 & 1 & 0 & 0 & 0 & 0 & 1 & 0 & 0 \\ 0 & 0 & 0 & 0 & 0 & 0 & 1 & 0 & 0 & 0 \\ 1 & 0 & 1 & 0 & 0 & 0 & 0 & 0 & 0 & 1 \\ 0 & 0 & 0 & 0 & 0 & 0 & 0 & 0 & 0 & 1 \\ 0 & 0 & 1 & 0 & 0 & 0 & 0 & 0 & 0 & 0 \\ 0 & 0 & 1 & 0 & 0 & 0 & 0 & 1 & 0 & 0 \end{bmatrix} \quad (B.12)$$

In other words, for each of the intensity pairs, such as (1, 2), we count the number of pixel pairs at relative distance (d=1) and orientation $\alpha$=0° (horizontal) that take these values. In our case this is 2. There are two instances in the image (B.11) where two, horizontally adjacent pixels have the values 1 and 2. The element (3, 5) in the GLCM is 3 because in the example image there are 3 instances in which two, horizontally adjacent pixels have the values 3 and 5. From the same image (B.11) and (d=1, $\alpha$=45°) we obtain:

$$GLCM^{45}(d=1) = \begin{bmatrix} 0 & 0 & 1 & 0 & 0 & 1 & 0 & 1 & 0 & 0 \\ 0 & 0 & 1 & 0 & 0 & 0 & 1 & 0 & 0 & 0 \\ 0 & 1 & 1 & 0 & 0 & 0 & 0 & 0 & 0 & 1 \\ 0 & 0 & 0 & 0 & 0 & 0 & 0 & 0 & 0 & 0 \\ 0 & 0 & 0 & 1 & 0 & 0 & 1 & 0 & 0 \\ 0 & 0 & 0 & 0 & 1 & 0 & 0 & 0 & 0 & 0 \\ 1 & 0 & 0 & 0 & 1 & 0 & 0 & 0 & 0 & 1 \\ 0 & 0 & 0 & 0 & 0 & 0 & 0 & 0 & 0 & 0 \\ 1 & 0 & 0 & 0 & 0 & 0 & 0 & 0 & 0 & 0 \\ 0 & 0 & 0 & 0 & 0 & 0 & 0 & 1 & 0 & 0 \end{bmatrix} \quad (B.13)$$

As illustrative example we will obtain the gray-level co-occurrence matrix from a given tumor image. FIG. 8 provides an example of a given gray scale ROI image (color map changed for better visual inspection) to the left, and a scaled version of the left image to 32 discrete gray levels to the right. In FIG. 8, the image in the left hand side corresponds to a given gray-level ROI image, the color map has been changed to enhance the differences for visual inspection. The image in the right corresponds to the scaled ROI with 32 discrete gray values. The co-occurrence matrices are obtained from the scaled image.

Having defined the probabilities of occurrence of gray levels with respect to relative spatial position we can define the relevant co-occurrence features that have been extracted; in some cases they have a direct physical interpretation with respect to the texture of an image, for example, they quantify coarseness, smoothness, randomness, etc. Others do not have such a property but they still encode highly discriminative texture-related information. Denoting by P(i,j) the normalized co-occurrence matrix, by $N_g$ the number of discrete gray levels of the image, the co-occurrence features relevant for our application are defined as follows:

10. Contrast $$Con = \sum_{n=1}^{N_g} n^2 \left\{ \frac{\sum_{i=1}^{N_g} \sum_{j=1}^{N_g} P(i,j)}{|i-j|=n} \right\} \quad (B.14)$$

This is a measure intensity contrast between a pixel and its neighbor over the entire image, that is, a measure of the local gray level variations. For a constant image this metric is zero. The $n^2$ dependence weights the big differences more.

11. Correlation $$\text{Correlation} = \sum_{i=1}^{N_g} \sum_{j=1}^{N_g} \frac{(i-\mu_i)(j-\mu_j)P(i,j)}{\sigma_i \sigma_j} \quad \text{(B. 15)}$$

This metric measure how correlated is a pixel to its neighbor over the entire image. Correlation takes the values 1 or −1 for perfectly positively or negatively correlated image.

12. Energy $$\text{Energy} = \Sigma_{i=1}^{N_g} \Sigma_{j=1}^{N_g} (P(i,j))^2 \quad \text{(B.16)}$$

Energy is the sum of the squared elements of an image and a measure of smoothness. If all pixels are of the same gray level then energy is equal to 1; at the other extreme if we have all possible pairs of gray levels with equal probability, the region is less smooth, with a more uniformly distributed $P(i,j)$ and a lower energy.

13. Homogeneity $$\text{Homogeneity} = \sum_{i=1}^{N_g} \sum_{j=1}^{N_g} \frac{P(i,j)}{1+|i-j|} \quad \text{(B. 17)}$$

This feature measures how close is the distribution of elements in the co-occurrence matrix to the diagonal of the co-occurrence matrix. Homogeneity is 1 for a constant image.

14. Inverse Difference Moment $$IDM = \sum_{i=1}^{N_g} \sum_{j=1}^{N_g} \frac{P(i,j)}{1+|i-j|^2} \quad \text{(B. 18)}$$

This feature takes high values for images with low contrast due to the $(i-j)^2$ dependence.

15. Sum Average $$SA = \Sigma_{i=2}^{2N_g}[i P_{x+y}(i)] \quad \text{(B.19)}$$

In A.18 $P_x(i)$ and $P_y(i)$ are the row and column marginal probabilities, obtained by summing the rows or columns $P(i,j)$.

16. Sum Variance $$SV = \Sigma_{i=2}^{2N_g}[(i-\text{sum average})^2 P_{x+y}(i)] \quad \text{(B.20)}$$

17. Sum Entropy $$SE = -\Sigma_{i=2}^{2N_g}[P_{x+y}(i) \log[P_{x+y}(i)]] \quad \text{(B.21)}$$

All the second-order statistics based features are functions of the distance d and the orientation a. Here for the direction d=1, the resulting values for the four directions are averaged. These metrics take into account the local intensity and spatial relationship of pixels over the region and are independent to tumor position, size, orientation and brightness.

Run-Length Gray-Level Statistics

Additionally we examined gray-level runs derived from run-length matrices (RLM) using a run-length metrics. A gray level run is a set of consecutive pixels having the same gray level value. The length of the run is the number of pixels in the run. Run length features describe textural information related with the number of times each gray level appears by itself, in pairs and so on, in a certain distance and orientation. Taking for example the image $$I = \begin{bmatrix} 5 & 2 & 5 & 4 & 4 \\ 3 & 3 & 3 & 1 & 3 \\ 2 & 1 & 1 & 1 & 3 \\ 4 & 2 & 2 & 2 & 3 \\ 3 & 5 & 3 & 3 & 2 \end{bmatrix} \quad \text{(B. 22)}$$

with five possible gray levels. For each of the previously defined angular directions (0°, 45°, 90° and 135°) the corresponding run length matrices are defined. The run length matrix is an $N_g \times N_r$ array where $N_r$ is the largest possible run length in the image. For distance (d=1) and orientation (a=0°) we obtain:

$$Q_{RL}(0°) = \begin{bmatrix} 1 & 0 & 1 & 0 & 0 \\ 3 & 0 & 1 & 0 & 0 \\ 4 & 1 & 1 & 0 & 0 \\ 1 & 1 & 0 & 0 & 0 \\ 3 & 0 & 0 & 0 & 0 \end{bmatrix} \quad \text{(B. 23)}$$

The element (1,1) of the run length matrix is the number of times that the gray level 1 appears by itself, the second element is the number of times it appears in pairs (zero in the example), and so on. The element (3,3) is the number of times the gray level 3 appears in the image with run length 3. For the diagonal direction we obtain:

$$Q_{RL}(45°) = \begin{bmatrix} 2 & 1 & 0 & 0 & 0 \\ 6 & 0 & 0 & 0 & 0 \\ 7 & 1 & 0 & 0 & 0 \\ 3 & 0 & 0 & 0 & 0 \\ 3 & 0 & 0 & 0 & 0 \end{bmatrix} \quad \text{(B. 24)}$$

Denoting by P the total number of pixels of an image, by $Q_{RL}(i,j)$ the (i,j)-th element of the run length matrix for a specific distance d and a specific angle a and by Nr the number of different runs that occur, based on the definition of the run length matrices, the following rung length features are defined:

18. Short Run Emphasis $$SRE = \frac{\sum_{i=1}^{N_g} \sum_{j=1}^{N_r} (Q_{RL}(i,j)/j^2)}{\sum_{i=1}^{N_g} \sum_{j=1}^{N_r} Q_{RL}(i,j)} \quad \text{(B. 25)}$$

This feature emphasizes small run lengths. The denominator is the number of run lengths in the matrix, for example, 17 in B.23 and 23 in B.24.

19. Long Run Emphasis $$LRE = \frac{\sum_{i=1}^{N_g} \sum_{j=1}^{N_r} (Q_{RL}(i,j) \cdot j^2)}{\sum_{i=1}^{N_g} \sum_{j=1}^{N_r} Q_{RL}(i,j)} \quad \text{(B. 26)}$$

In this case long run lengths are emphasized. For smoother images RLE should take larger values while SRE takes larger values with coarser image.

20. Gray Level Non-Uniformity $$SRE = \frac{\sum_{i=1}^{N_g}\left[\sum_{j=1}^{N_r} Q_{RL}(i,j)\right]^2}{\sum_{i=1}^{N_g}\sum_{j=1}^{N_r} Q_{RL}(i,j)} \quad (B.27)$$

This feature takes small values when the runs are uniformly distributed among the gray levels.

21. Run Percentage $$RP = \frac{\sum_{i=1}^{N_g}\sum_{j=1}^{N_r} Q_{RL}(i,j)}{P} \quad (B.28)$$

Run percentage takes high values for coarse images. For each angular direction, the complete set of second-order statistics and run-length features was computed but only the average value was used as feature.

Shape and Size Based Features

We extended the number of extracted image traits by adding measurements of the size and shape of the tumor region. For every two-dimensional image of the tumor in a given CT stack three features are obtained, maximum cross-sectional area, perimeter and mayor axis length as follows:

22. Area

We count the number of pixels in the ROI's and the maximum count is denoted as the maximum cross-sectional area.

23. Perimeter

Is the distance between each adjoining pair of pixels around the border of the region; the total sum of the perimeters for each ROI image is taken as feature.

24. Mayor Axis Length

This feature specifies the maximum length in pixels of the mayor axis of a two-dimensional ROI image.

25. Volume

The total volume of the tumor is determined by counting the number of pixels in the tumor region and multiplying this value by the voxel size. The voxel size is obtained from the PixelSpacing section of the CT Dicom Header which specifies the size of a voxel in the x, y, and z directions. The result is a value in mm$^3$. Based on the CT-GTV volume that was described above, 3D representations of the tumor volume have been rendered.

26. Maximum Diameter

In contrast with the mayor axis-length which was determined in two-dimensional ROI images, this feature examines the maximum diameter of the tumor region in a three-dimensional space. Firstly, we obtain the coordinates of all the points located at the surface of the tumor region; secondly, the distance between each pair of points in the tumor contour is determined using the following metric called "City Bloc Distance":

$$D = |x_1 - x_2| + |y_1 - y_2| + |z_1 - z_2| \quad (B.29)$$

The points in the tumor contour whose edges touch are 1 unit apart; points diagonally touching are separated by two units. The two points with the maximum distance are the points at the edges of the maximum diameter. In FIG. 3, as referred to above, a plot of the points in the surface of a given tumor volume is shown; the maximum diameter is calculated among the points in this image.

So far we have described the extraction of image traits regarding the gray level and spatial relationship between pixels in a region, as well as size measurements of the tumor region in two and three-dimensions. Another important issue in the task of patter recognition is the analysis of shape; in this regard the extracted image traits are completed by adding the following three shape-based features:

27. Surface to Volume Ratio.

This feature is intended to express how spiky or sharp is the tumor volume. A more lobulated tumor volume would result in a higher surface to volume ratio. To calculate this feature first we determine and count the pixels located at the surface of the tumor (e.g. as shown in FIGS. 2A-1 and 2B-1); the resulting number is divided by the sum of all the pixels in the tumor volume.

28. Sphericity

This is a measure of how spherical or rounded is the shape of the tumor volume. Defined in [16], the sphericity of an object is the ratio of the surface area of a sphere (with the same volume as the given object) to the surface area of the object:

$$\Psi = \frac{\pi^{\frac{1}{3}}(6V)^{\frac{2}{3}}}{A} \quad (B.30)$$

Where A and V are the surface area and volume of the tumor respectively as determined for the surface to volume ratio.

29. Compactness

This is an intrinsic characteristic of the shape of objects that has been widely used in pattern recognition tasks and represents the degree to which a shape is compact. The compactness of a three-dimensional tumor volume is obtained as follows:

$$Comp = \frac{V}{\sqrt{\pi}\, A^{2/3}} \quad (B.31)$$

The similarity to a sphere and compactness features are dimensionless numbers and they are independent to scaling and orientation. The feature generation phase of this methodology can be performed in a semi-fully automated fashion since the tumor delineations carried out by the physician are needed by the algorithm. The features enlisted in this appendix will be fed to a classifier as inputs in the learning and recognition phase of the classification task.

Image Feature Parameter Description (Part 2)

Additional First Order Gray-Level Statistics

In this section various further image feature parameters in the class first order gray-level statistics are described, which are additional to the parameters described in section 'Image feature parameter description (part 1)', sub-section 'First order gray-level statistics'. Herein, I(x,y,z) represents a standard uptake value (SUV) or intensity of a voxel, i.e. a voxel value taken from the image data directly.

30. Energy

This feature is described by the following equation:

$$E_{tot} = V_{voxel} \sum_{x=1}^{x} \sum_{y=1}^{y} \sum_{z=1}^{z} I(x,y,z)^2 \quad (B.32)$$

Where $V_{voxel}$ is the voxel volume of the three dimensional image. The voxel volume is the product of the pixel spacing in x-direction, the pixel spacing in y-direction and the pixel spacing in z-direction. Total Energy is normalized by the voxel volume.

31. Mean Absolute Deviation

This feature equals the mean of the absolute deviations of all voxel intensities around the mean intensity value represented by image feature parameter 4 (equation B.4) above.

32. Median

Median is a well known statistical parameter, indicating in this case the median intensity value.

33. Root Mean Square

Root mean square is a well known statistical parameter, indicating in this case the quadratic mean, or the square root of the mean of squares of all voxel intensities.

34. SUV Peak

This image feature parameter is defined as the mean standard uptake value (SUV) within a 1 cm³ sphere centered around the maximum SUV voxel.

35. Uniformity

Let P define the first order histogram and P(i) the fraction of voxels with intensity level i. $N_l$ is the number of discrete intensity levels. Then:

$$\text{uniformity} = \sum_{i=1}^{N_l} P(i)^2$$

Additional Shape and Size Based Features

Below, a number of further shape and size (i.e. geometric) features are described, in addition to those features described as image feature parameter numbers 22 to 29 above, describing the shape and size of the volume of interest. Let V be the volume and A be the surface area of interest.

36. Compactness Second Type ('Compactness 2')

Compactness second type is an alternative image feature parameter that relates to the compactness of the neoplasm considered. This parameter is described by:

$$\text{compactness 2} = 36\pi \frac{V^2}{A^3}$$

37. Spherical Disproportion

Where R is the radius of a sphere with the same volume as the tumor, the spherical disproportion is:

$$\text{spherical disproportion} = \frac{A}{4\pi R^2}$$

38. Maximum 3D Diameter

This parameter equals the maximum three dimensional tumor diameter measurable from the image.

Additional Second-Order Gray Levels Statistics

These additional features are again based on the gray-level co-occurrence matrices. Recalling from the above description of the co-occurrence matrices, let:

P(i,j) be the co-occurrence matrix,
$N_g$ be the number of discrete intensity levels in the image,
μ be the mean of P(i,j),
$\mu_x(i)$ be the mean of row i,
$\mu_y(j)$ be the mean of column j,
$\sigma_x(i)$ be the standard deviation of row i,
$\sigma_y(j)$ be the standard deviation of column j,
$p_x(i) = \sum_{j=1}^{N_g} P(i,j)$,
$p_y(i) = \sum_{i=1}^{N_g} P(i,j)$,
$p_{x+y}(k) = \sum_{i=1}^{N_g} \sum_{j=1}^{N_g} P(i,j)$, i+j=k, k=2, 3, ..., $2N_g$,
$p_{x-y}(k) = \sum_{i=1}^{N_g} \sum_{j=1}^{N_g} P(i,j)$, |i−j|=k, k=0, 1, ..., $N_g - 1$,
HXY1 = $-\sum_{i=1}^{N_g} \sum_{j=1}^{N_g} P(i,j) \log(p_x(i)p_y(j))$,
HXY2 = $-\sum_{i=1}^{N_g} \sum_{j=1}^{N_g} p_x(i)p_y(j) \log(p_x(i)p_y(j))$.

Then the following further image feature parameters are included in this class.

39. Autocorrelation $$\text{autocorrelation} = \sum_{i=1}^{N_g} \sum_{j=1}^{N_g} ijP(i,j)$$

40. Cluster Prominence:

$$\text{cluster prominence} = \sum_{i=1}^{N_g} \sum_{j=1}^{N_g} [i + j - \mu_x(i) - \mu_y(j)]^4 P(i,j)$$

41. Cluster Shade:

$$\text{cluster shade} = \sum_{i=1}^{N_g} \sum_{j=1}^{N_g} [i + j - \mu_x(i) - \mu_y(j)]^3 P(i,j)$$

42. Cluster Tendency:

$$\text{cluster tendency} = \sum_{i=1}^{N_g} \sum_{j=1}^{N_g} [i + j - \mu_x(i) - \mu_y(j)]^2 P(i,j)$$

43. Difference Entropy $$\text{difference entropy} = \sum_{i=0}^{N_g - 1} P_{x-y}(i) \log_2[P_{x-y}(i)]$$

44. Dissimilarity $$\text{dissimilarity} = \sum_{i=1}^{N_g} \sum_{j=1}^{N_g} |i - j| P(i,j)$$

45. Homogeneity Second Type

This parameter relates to an alternative manner of describing the homogeneity.

$$\text{homogeneity 2} = \sum_{i=1}^{N_g} \sum_{j=1}^{N_g} \frac{P(i,j)}{1 + |i - j|^2}$$

46. Entropy $$\text{entropy} = -\sum_{i=1}^{N_g} \sum_{j=1}^{N_g} P(i,j) \log_2[P(i,j)]$$

47. Informational Measure of Correlation 1 (IMC1):

$$IMC1 = \frac{H - HXY1}{\max\{HX, HY\}}$$

Where H is the entropy.

48. Informational Measure of Correlation 2 (IMC2):

$$IMC2 = \sqrt{1 - e^{-2(HXY2-H)}}$$

Where H is the entropy.

49. Inverse Difference Moment Normalized (IDMN):

$$IDMN = \sum_{i=1}^{N_g} \sum_{j=1}^{N_g} \frac{P(i,j)}{1 + \left(\frac{|i-j|^2}{N^2}\right)}$$

50. Inverse Difference Normalized (IDN):

$$IDN = \sum_{i=1}^{N_g} \sum_{j=1}^{N_g} \frac{P(i,j)}{1 + \left(\frac{|i-j|}{N}\right)}$$

51. Inverse Variance:

$$\text{inverse variance} = \sum_{i=1}^{N_g} \sum_{j=1}^{N_g} \frac{P(i,j)}{|i-j|^2}, i \neq j$$

52. Maximum Probability:

$$\text{maximum probability} = \max\{P(i,j)\}$$

53. Variance:

$$\text{variance} = \sum_{i=1}^{N_g} \sum_{j=1}^{N_g} (i-\mu)^2 P(i,j)$$

Additional Run-Length Gray-Level Statistics

Additional run length matrix based features are defines below. In the equations below, we denote $p(i,j|\theta)$ to be the $(i,j)^{th}$ entry in the given run-length matrix p for a direction $\theta$. Thus $p(i,j|\theta)$ as denoted in the equations below equals the earlier defined $Q_{RL}(\theta)$, the run length matrix in direction $\theta$.

54. Run Length Non-Uniformity (RLN)

$$RLN = \frac{\sum_{j=1}^{N_r} \left[\sum_{i=1}^{N_g} p(i,j|\theta)\right]^2}{\sum_{i=1}^{N_g} \sum_{j=1}^{N_r} p(i,j|\theta)}$$

55. Low Gray Level Run Emphasis (LGLRE)

$$LGLRE = \frac{\sum_{i=1}^{N_g} \sum_{j=1}^{N_r} \left[\frac{p(i,j|\theta)}{i^2}\right]}{\sum_{i=1}^{N_g} \sum_{j=1}^{N_r} p(i,j|\theta)}$$

56. High Gray Level Run Emphasis (HGLRE)

$$HGLRE = \frac{\sum_{i=1}^{N_g} \sum_{j=1}^{N_r} i^2 p(i,j|\theta)}{\sum_{i=1}^{N_g} \sum_{j=1}^{N_r} p(i,j|\theta)}$$

57. Short Run Low Gray Level Emphasis (SRLGLE)

$$SRLGLE = \frac{\sum_{i=1}^{N_g} \sum_{j=1}^{N_r} \left[\frac{p(i,j|\theta)}{i^2 j^2}\right]}{\sum_{i=1}^{N_g} \sum_{j=1}^{N_r} p(i,j|\theta)}$$

58. Short Run High Gray Level Emphasis (SRHGLE)

$$SRHGLE = \frac{\sum_{i=1}^{N_g} \sum_{j=1}^{N_r} \left[\frac{p(i,j|\theta) i^2}{j^2}\right]}{\sum_{i=1}^{N_g} \sum_{j=1}^{N_r} p(i,j|\theta)}$$

59. Long Run Low Gray Level Emphasis (LRLGLE)

$$LRLGLE = \frac{\sum_{i=1}^{N_g} \sum_{j=1}^{N_r} \left[\frac{p(i,j|\theta) j^2}{i^2}\right]}{\sum_{i=1}^{N_g} \sum_{j=1}^{N_r} p(i,j|\theta)}$$

60. Long Run High Gray Level Emphasis (LRHGLE)

$$LRHGLE = \frac{\sum_{i=1}^{N_g} \sum_{j=1}^{N_r} p(i,j|\theta) i^2 j^2}{\sum_{i=1}^{N_g} \sum_{j=1}^{N_r} p(i,j|\theta)}$$

Gray-Level Size-Zone Matrix Based Features

A further class of image feature parameters relate to the gray-level size zone matrix (GLSZM), which will first be briefly introduced herewith. The $(i,j)^{th}$ entry of the GLSZM $p(i,j)$ describes the number of connected areas of gray-level (i.e. intensity value) i and size j. GLSZM features therefore describe homogeneous areas within a tumor volume, describing tumor heterogeneity at a regional scale.

Taking for example the image with five possible gray-levels:

$$I = \begin{bmatrix} 5 & 4 & 4 & 2 & 2 \\ 1 & 4 & 2 & 2 & 5 \\ 1 & 1 & 3 & 3 & 3 \\ 2 & 2 & 3 & 3 & 1 \\ 2 & 2 & 2 & 1 & 1 \end{bmatrix}$$

The resulting GLSZM will then be:

$$p = \begin{bmatrix} 0 & 0 & 2 & 0 & 0 \\ 0 & 0 & 0 & 1 & 1 \\ 0 & 0 & 0 & 0 & 1 \\ 0 & 0 & 1 & 0 & 0 \\ 2 & 0 & 0 & 0 & 0 \end{bmatrix}$$

In the above example, both $p(1,1)$ equals 0 because there are no regions of gray-level value 1 with only one connected area; while $p(1,3)$ equals 2, because there are two regions with three connected areas of gray level 1. In three dimensions, voxels of the same gray-level are considered to be connected (i.e. belonging to the same area) if they are part of a 26-connected neighborhood.

Let: $p(i,j)$ be the $(i,j)$th entry in the given GLSZM p; $N_g$ the number of discrete intensity values in the image; $N_z$ the size of the largest, homogeneous region in the volume of interest; $N_a$ the number homogeneous areas in the image.

61. Small Area Emphasis (SAE)

$$SAE = \frac{\sum_{i=1}^{N_g} \sum_{j=1}^{N_z} \left[\frac{p(i,j)}{j^2}\right]}{\sum_{i=1}^{N_g} \sum_{j=1}^{N_z} p(i,j)}$$

62. Large Area Emphasis (LAE)

$$LAE = \frac{\sum_{i=1}^{N_g} \sum_{j=1}^{N_z} j^2 p(i,j)}{\sum_{i=1}^{N_g} \sum_{j=1}^{N_z} p(i,j)}$$

63. Intensity Variability (IV)

$$IV = \frac{\sum_{i=1}^{N_g} \left[\sum_{j=1}^{N_z} p(i,j)\right]^2}{\sum_{i=1}^{N_g} \sum_{j=1}^{N_z} p(i,j)}$$

64. Size-Zone Variability (SZV)

$$SZV = \frac{\sum_{j=1}^{N_z} \left[\sum_{i=1}^{N_g} p(i,j)\right]^2}{\sum_{i=1}^{N_g} \sum_{j=1}^{N_z} p(i,j)}$$

65. Zone Percentage (ZP)

$$ZP = \sum_{i=1}^{N_g} \sum_{j=1}^{N_z} \frac{p(i,j)}{N_a}$$

66. Low Intensity Emphasis (LIE)

$$LIE = \frac{\sum_{i=1}^{N_g} \sum_{j=1}^{N_z} \left[\frac{p(i,j)}{i^2}\right]}{\sum_{i=1}^{N_g} \sum_{j=1}^{N_z} p(i,j)}$$

67. High Intensity Emphasis (HIE)

$$HIE = \frac{\sum_{i=1}^{N_g} \sum_{j=1}^{N_z} i^2 p(i,j)}{\sum_{i=1}^{N_g} \sum_{j=1}^{N_z} p(i,j)}$$

68. Low Intensity Small Area Emphasis (LISAE)

$$LISAE = \frac{\sum_{i=1}^{N_g} \sum_{j=1}^{N_z} \left[\frac{p(i,j)}{i^2 j^2}\right]}{\sum_{i=1}^{N_g} \sum_{j=1}^{N_z} p(i,j)}$$

69. High Intensity Small Area Emphasis (HISAE)

$$HISAE = \frac{\sum_{i=1}^{N_g} \sum_{j=1}^{N_z} \left[\frac{p(i,j) i^2}{j^2}\right]}{\sum_{i=1}^{N_g} \sum_{j=1}^{N_z} p(i,j)}$$

70. Low Intensity Large Area Emphasis (LILAE)

$$LILAE = \frac{\sum_{i=1}^{N_g} \sum_{j=1}^{N_z} \left[\frac{p(i,j)j^2}{i^2}\right]}{\sum_{i=1}^{N_g} \sum_{j=1}^{N_z} p(i,j)}$$

71. High Intensity Large Area Emphasis (HILAE)

$$HILAE = \frac{\sum_{i=1}^{N_g} \sum_{j=1}^{N_z} p(i,j) i^2 j^2}{\sum_{i=1}^{N_g} \sum_{j=1}^{N_z} p(i,j)}$$

Intensity Volume Histogram (IVH) Features (PET Only)

Where the imaging method used is positron emission tomography (PET), a further class of image features of interest is based on the intensity volume histogram of the PET image. The intensity volume histogram summarizes the complex three dimensional (3D) data contained in the image into a single curve, allowing for a simplified interpretation.

The image feature parameters below relate to relative volumes or intensities (denoted by x), absolute intensities (denoted by y) and/or absolute volumes (denoted by z). Relative steps in volume and intensity (x) were taken in 10% increments; x={10%, 20%, . . . , 90%}. Absolute steps in intensity (y) were taken in 0.5 [SUV]; y={0.5, 1, . . . , SUVmax}, where SUVmax is the maximum image intensity value. Absolute steps in volume (z) were taken in 0.5 ml increments; z={0.5 ml, 1 ml, . . . , V}, where V is the tumor volume.

The following image feature parameters may be applied.

72. $AVAI_y$

Volume (AV) [ml] above (i.e. with at least) an intensity (AI).

73. $RVAI_y$

Relative volume (RV) [%] above (i.e. with at least) an intensity (AI).

74. $AVRI_x$

Volume (AV) [ml] above (i.e. with at least) a relative intensity (RI).

75. $RVRI_x$

Relative volume (RV) [%] above (i.e. with at least) a relative intensity (RI).

76. $AIAV_z$

Intensity thresholds (AI) [SUV] for the Z ml highest intensity volume (AV).

77. $AIRV_x$

Intensity thresholds (AI) [SUV] for the X % highest intensity volume (RV).

78. $MIAV_z$

Mean intensity (MI) [SUV] in the Z ml highest intensity volume (AV).

79. $MIRV_x$

Mean intensity (MI) [SUV] in the X % highest intensity volume (RV).

80. $TLGAI_y$

Total lesion glycolysis (TLG) for volume (TLG) above (i.e. with at least) an intensity (AI).

81. $TLGRI_x$

Total lesion glycolysis (TLG) for volume (TLG) above (i.e. with at least) a relative intensity (RI).

Wavelet Transforms of Image Feature Parameters

The features described in this document may further be utilized by performing a wavelet transform on the images. By taking the wavelet transformed image data as input, in addition to the untransformed image data, a complete new set of image feature parameters is obtained that can be used to obtain the predictive value in a method in accordance with the present invention.

Figure 9:
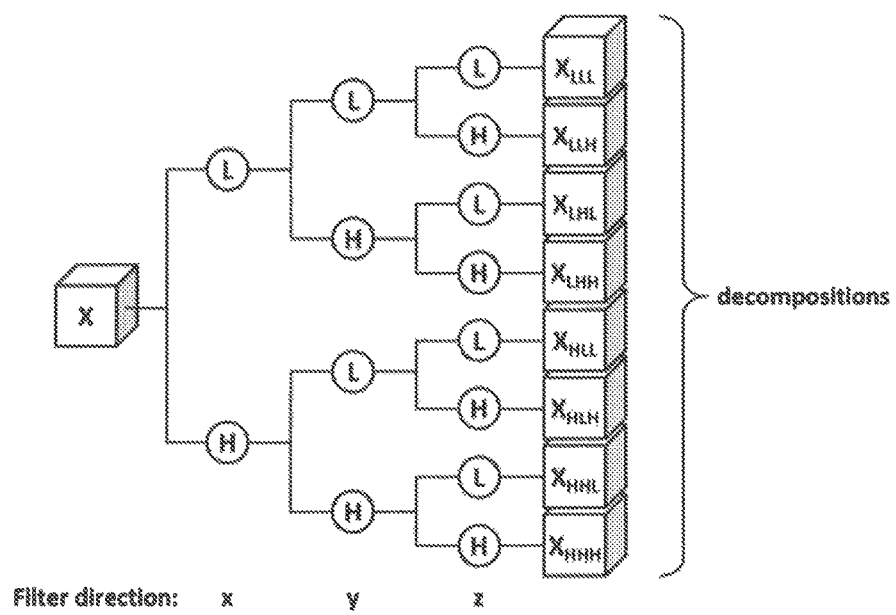
FIG. 9 schematically illustrate decomposition using a wavelet transform.

Wavelet transform effectively decouples textural information by decomposing the original image, in a similar manner as Fourier analysis, in low and high-frequencies. For example, a discrete, one-level and undecimated three dimensional wavelet transform may be applied to a CT image, which decomposes the original image X into 8 decompositions. Consider L and H to be a low-pass (i.e. a scaling) and, respectively, a high-pass (i.e. a wavelet) function, and the wavelet decompositions of X to be labeled as $X_{LLL}$, $X_{LLH}$, $X_{LHL}$, $X_{LHH}$, $X_{HLL}$, $X_{HLH}$, $X_{HHL}$ and $X_{HHH}$. For example, $X_{LLH}$ is then interpreted as the high-pass sub band, resulting from directional filtering of X with a low-pass filter along x-direction, a low pas filter along y-direction and a high-pass filter along z-direction and is constructed as:

$$X_{LLH}(i,j,k) = \sum_{p=1}^{N_L} \sum_{q=1}^{N_L} \sum_{r=1}^{N_H} L(p)L(q)H(r)X(i+p, j+q, k+r)$$

Where $N_L$ is the length of filter L and $N_H$ is the length of filter H. The other decompositions are constructed in a similar manner, applying their respective ordering of low or high-pass filtering in x, y and z-direction. Wavelet decomposition of the image X is schematically depicted in FIG. 9. Since the applied wavelet decomposition is undecimated, the size of each decomposition is equal to the original image and each decomposition is shift invariant. Because of these properties, the original tumor delineation of the gross tumor volume (GTV) can be applied directly to the decompositions after wavelet transform.

The wavelet transform is a time-frequency-transformation based on a wavelet series. Wavelet series are a representation of a square-integrable (real- or complex-valued) function by a certain orthonormal series generated by a wavelet. This representation is performed on a Hilbert basis defined by orthonormal wavelets. The wavelet transform provides information similar to the short-time-Fourier-transformation, but with additional special properties of the wavelets, which show up at the resolution in time at higher analysis frequencies of the basis function. Wavelet transforms provide the frequency of the signals and the time associated to those frequencies. High-low-high filtering applies to data analysis methods relying on wavelet transforms to detect certain activity patterns or variation patterns in the data; the high-low-high is thereby indicative of the wavelet shape. The transform is applied directly on the raw CT image.

In the above description, the invention is described with reference to some specific embodiments thereof. However, it will be appreciated that the present invention may be practiced otherwise than specifically described herein, in relation to these embodiments. Variations and modifications to specific features of the invention may be apparent to the skilled reader, and are intended to fall within the scope of the invention. The scope of the invention is merely restricted by the scope of the appended claims.

The invention claimed is:

1. An image analysis method for providing information for supporting illness development prediction regarding a neoplasm in a human or animal body, the method comprising:
receiving, by a processing unit, image data of the neoplasm, wherein said receiving comprises:
receiving first image data of the neoplasm at a first moment in time, and
receiving second image data of the neoplasm at a second moment in time;
deriving, by the processing unit, for each of a plurality of image features associated with the neoplasm:
a first image feature parameter value from the first image data, and
a second image feature parameter value from the second image data,
said first image feature parameter value and second image feature parameter value being a quantitative representation of said respective image feature at said first and second moment in time respectively; and
calculating, by the processing unit, for each one of the plurality of image features, an image feature difference value by calculating a difference between the first image feature parameter value and the second image feature parameter value for said one of the plurality of image features;
wherein the method further includes:
deriving, by said processing unit using a prediction model, a predictive value associated with the neoplasm for supporting treatment thereof, wherein said prediction model includes a plurality of multiplier values, each one of the plurality of multiplier values being associated with an image feature for multiplying an associated image feature difference value therewith, and
wherein calculating, during the deriving, the predictive value associated with the neoplasm includes:
multiplying each image feature difference value with its associated multiplier value, and
combining the multiplied image feature difference values to obtain the predictive value associated with the neoplasm.

2. The image analysis method according to claim 1, wherein the first and second image feature parameter values are quantitative values obtained from said first and second image data and associated with image feature parameters, the image feature parameters being one or more elements of the group consisting of:
first-order gray level statistics obtained from image pixels or areas of the image from the image data;
second-order gray level statistics obtained from co-occurrence matrices of the image data;
shape and size based features; and
intensity volume histogram based features of positron emission tomography images.

3. The image analysis method according to claim 1, wherein calculating an image feature difference value comprises calculating an image feature difference percentage.

4. The image analysis method according to claim 1, wherein the multiplier values include one or more weighing factors associated with the image features, wherein the weighing factors indicate an importance of the respective image features for obtaining the predictive value.

5. The image analysis method according to claim 1, wherein the multiplier values include one or more selector values associated with the image features, and wherein the selector values indicate whether the associated image features are to be included for obtaining the predictive value.

6. The image analysis method according to claim 1, wherein the image data is obtained using at least one of the group consisting of:
a computed tomography imaging method,
a positron emission tomography method,
a magnetic resonance imaging method, a single photon emission computed tomography imaging method,
a planar gamma imaging method,
an ultrasonography imaging method,
a thermography imaging method, and
a photo-acoustic imaging method.

7. The image analysis method according to claim 1, wherein the image data is obtained using a computed tomography imaging method, and wherein the first and second image feature parameter values are quantitative values obtained from said first and second image data and associated with image feature parameters, the image feature parameters including at least:
a high-high-low filtered wavelet transform of the parameter kurtosis from the class first level statistics; and
a high-low-low filtered wavelet transform of the parameter homogeneity second type from the class second order gray-level statistics.

8. The image analysis method according to claim 7, wherein the multiplier values are represented by hazard ratios associated with the image feature parameters, the prediction model including:
for the high-high-low filtered wavelet transform of the parameter kurtosis a hazard ratio—HR—between 0.980 and 0.995; and
for the high-low-low filtered wavelet transform of the parameter homogeneity second type a hazard ratio— HR—between 1.005 and 1.020.

9. The image analysis method according to claim 1, wherein the image data is obtained using a computed tomography imaging method, and wherein the first and second image feature parameter values are quantitative values obtained from said first and second image data and associated with image feature parameters, the image feature parameters including at least:
the parameter run-length non-uniformity from the class run-length gray-level statistics;
the parameter uniformity from the class first order statistics; and
a high-low-high filtered wavelet transform of the parameter normalized inverse difference moment from the class second order gray-level statistics.

10. The image analysis method according to claim 9, wherein the multiplier values are represented by hazard ratios associated with the image feature parameters, the prediction model including:
for the parameter run-length non-uniformity a hazard ratio—HR—between 1.01 and 1.10;
for the parameter uniformity a hazard ratio—HR—between 1.005 and 1.020; and
for the high-low-high filtered wavelet transform of the parameter normalized inverse difference moment a hazard ratio—HR—between 1.09 and 4.10.

11. The image analysis method according to claim 1, wherein the image data is obtained using a positron emission tomography imaging method, and wherein the first and second image feature parameter values are quantitative values obtained from said first and second image data and associated with image feature parameters, the image feature parameters including at least:

the parameter entropy from the class first level statistics; and the parameter root mean square from the class first level statistics.

12. The image analysis method according to claim 11, wherein the multiplier values are represented by hazard ratios associated with the image feature parameters, the prediction model including:

for the parameter entropy a hazard ratio—HR—between 0.9 and 1.0, preferably HR=0.95;

for the parameter root mean square a hazard ratio—HR—between 1.01 and 1.05, preferably HR=1.03.

13. The image analysis method according to claim 1, wherein the image data is obtained using a positron emission tomography imaging method, wherein the first and second image feature parameter values are quantitative values obtained from said first and second image data and associated with image feature parameters, and wherein the image feature parameters include at least:

the parameter absolute intensity of a part of a volume of the neoplasm determined using an intensity volume histogram of said image data;

the parameter total lesion glycolysis for a volume of the neoplasm having an absolute intensity above a threshold determined using an intensity volume histogram of said image data; and the parameter uniformity from the class first order statistics.

14. The image analysis method according to claim 13, wherein the multiplier values are represented by hazard ratios associated with the image feature parameters, the prediction model including:

for the parameter absolute intensity of a part of a volume of the neoplasm, a hazard ratio—HR—between 1.01 and 1.05;

for the parameter total lesion glycolysis for a volume of the neoplasm having an absolute intensity above a threshold, a hazard ratio—HR—between 0.97 and 1.01; and for the parameter uniformity a hazard ratio—HR—between 0.99 and 1.03.

15. A non-transitory computer-readable medium comprising computer-executable instructions that, when executed by a computer, perform an image analysis method comprising:

receiving, by a processing unit, image data of the neoplasm, wherein said receiving comprises:

receiving first image data of the neoplasm at a first moment in time, and receiving second image data of the neoplasm at a second moment in time;

deriving, by the processing unit, for each of a plurality of image features associated with the neoplasm:

a first image feature parameter value from the first image data, and a second image feature parameter value from the second image data, said first image feature parameter value and second image feature parameter value being a quantitative representation of said respective image feature at said first and second moment in time respectively; and calculating, by the processing unit, for each one of the plurality of image features, an image feature difference value by calculating a difference between the first image feature parameter value and the second image feature parameter value for said one of the plurality of image features;

wherein the method further includes:

deriving, by said processing unit using a prediction model, a predictive value associated with the neoplasm for supporting treatment thereof, wherein said prediction model includes a plurality of multiplier values, each one of the plurality of multiplier values being associated with an image feature for multiplying an associated image feature difference value therewith, and wherein calculating, during the deriving, the predictive value associated with the neoplasm includes:

multiplying each image feature difference value with its associated multiplier value, and combining the multiplied image feature difference values to obtain the predictive value associated with the neoplasm.

* * * * *